(12) United States Patent
Jing et al.

(10) Patent No.: US 7,119,078 B2
(45) Date of Patent: Oct. 10, 2006

(54) TECHNOLOGY OF INTRACELLULAR DELIVERY OF DNA OLIGONUCLEOTIDES TO IMPROVE DRUG ACTIVITY

(75) Inventors: Naijie Jing, Pearland, TX (US); Weijun Xiong, Missouri City, TX (US); Yongli Guan, Pearland, TX (US)

(73) Assignee: Baylor College of Medicine, Houston, TX (US)

( * ) Notice: Subject to any disclaimer, the term of this patent is extended or adjusted under 35 U.S.C. 154(b) by 244 days.

(21) Appl. No.: 10/107,746

(22) Filed: Mar. 27, 2002

(65) Prior Publication Data

US 2006/0199777 A1   Sep. 7, 2006

Related U.S. Application Data

(60) Provisional application No. 60/278,942, filed on Mar. 27, 2001.

(51) Int. Cl.
*A01N 43/04*   (2006.01)
*C12Q 1/68*   (2006.01)
*C12N 15/88*   (2006.01)
*C07H 21/02*   (2006.01)
*C12P 19/34*   (2006.01)

(52) U.S. Cl. ............ 514/44; 435/6; 435/91.1; 435/455; 435/458; 536/23.1

(58) Field of Classification Search ............ 435/6, 435/91.1, 375, 455, 458; 536/23.1; 514/44
See application file for complete search history.

(56) References Cited

U.S. PATENT DOCUMENTS 6,040,181 A * 3/2000 Reed ............ 435/377
6,288,042 B1 * 9/2001 Rando et al. .......... 514/44

FOREIGN PATENT DOCUMENTS

WO   WO 97/20924   * 6/1997

OTHER PUBLICATIONS

M. Nielsen et al. Eur. J. Immunol. vol. 24, pp. 3082-3086 (1994).*
J. E. Darnell, Jr. Science, vol. 77, pp. 1630-1635 (1997).*
R. Tam et al. J. Immunol. vol. 163, No. 8, pp. 200-208 (1997).*
A. Peracchi et al. Rev. Med. Virol. vol. 14, pp. 47-64 (2004).*
A. Branch, Trends in Biochem. Sci. vol. 23, pp. 45-50 (1998).*
C. A. Stoddart et al. Antimicrobial Agents & Chemotherapy, vol. 42, No. 8, pp. 2113-2115 (1998).*
P. J. Bates et al. J. Biol. Chem. vol. 274, No. 37, pp. 26,369-26,377 (1999).*
P. J. Bates, et al. Proc. Am. Assoc. Cancer Res. Ann. Mtg. vol. 39, p. 64, Abstract No. 436 (1998).*
T. Chirila et al. Biomaterials, vol. 23, pp. 321-342 (2002).*
S. Crooke, Antisense Res. and Application, Chapter 1, pp. 1-50, S. Crooke, ed. Publi. Springer-Verlag (1998).*
N. Jing, Expert Opinion on Investigational Drugs, vol. 9, No. 8, pp. 1777-1785 (2000).*
S. Agrawal et al. Molecular Med. Today, vol. 61, pp. 72-81 (2000).*
Jing, Naijie, et al.; Rational Drug Design of DNA Oligonucleotides as HIV Inhibitors; Current Drug Targets—Infectious Disorders, 2001, 1, 79-90.
Jing, Naijie, et al.; Potassium-Induced Loop Conformational Transition of a Potent Anti-HIV Oligonucleotide; Journal of Biomolecular Structure & Dynamics, vol. 15 (3), pp. 573-585, 1997.
Jing, Naijie, et al.; Potassium-Dependent Foldling: A Key to Intracellular Delivery of G-Quartet Oligonucleotides as HIV Inhibitors; Biochemistry, vol. 41 (17), pp. 5397-5403, 2002.
Jing, Naijie, et al.; Structure-Activity of Tetrad-forming Oligonucleotides as a Potent Anti-HIV Therapeutic Drug; The Journal of Biological Chemistry, vol. 273 (52), pp. 34992-34999, Dec. 25, 1998.
Wang, Die, et al.; Stearylamine Liposome as a New Efficient Reagent for DNA Transfection of Eukaryotic Cells; Biochemical and Biophysical Research Communications 226, pp. 450-455, 1996.
Jing, Naijie, et al.; Stability-Activity Relationships of a Family of G-tetrad Forming Oligonucleotides as Potent HIV Inhibitors; The Journal of Biological Chemistry; vol. 275 (5), pp. 3421-3430, Feb. 4, 2000.
Jing, Naijie, et al.; Mechanism of Inhibition of HIV-1 Integrase by G-tetrad-forming Oligonucleotides in Vitro; The Journal of Biological Chemistry, vol. 275 (28), pp. 21460-21467, Jul. 14, 2000.
Jing, Naijie, et al.; Ion Selective Folding of Loop Domains in a Potent Anti-HIV Oligonucleotide; Biochemistry, vol. 36 (41), pp. 12498-12505, 1997.

* cited by examiner

*Primary Examiner*—Jane Zara
(74) *Attorney, Agent, or Firm*—Fulbright & Jaworski L.L.P.

(57) ABSTRACT

The present invention relates to methods of intracellular delivery of oligonucleotides. More particularly, the present invention relates to the use of the delivery system to deliver G-quartet oligonucleotides as a cancer therapy or an antiviral therapy.

15 Claims, 18 Drawing Sheets

A.

B.

TECHNOLOGY OF INTRACELLULAR DELIVERY OF DNA OLIGONUCLEOTIDES TO IMPROVE DRUG ACTIVITY

The present invention claims priority to U.S. Provisional Application No. 60/278,942, which was filed on Mar. 27, 2001.

The work herein was supported by grants from the United States Government. The United States Government may have certain rights in this invention.

BACKGROUND OF THE INVENTION

1. Field of Invention

The present invention relates to methods of intracellular delivery of oligonucleotides. Yet further, the present invention relates to the use of the delivery system to deliver G-quartet oligonucleotides as a cancer therapy or an antiviral therapy.

2. Related Art

The G-rich oligonucleotides have been identified, cloned and characterized in the telomeric sequences of many organisms, such as fungi, ciliates, vertebrates and insects (Henderson, 1995). The main structural motif of telomeric DNA is the G-quartet structure, which was first proposed by Cellert et al., 1962. The G-quartet consists of four guanine bases in a sequence array arranged into a cyclic Hoogsteen H-bonding structure and each G-base makes two H-bonds with its neighbor G-base (N1 to O6 and N2 to N7). G-quartets stack on top of each other to form tetrad-helical structures. The uniquely structural feature of G-quartet is a pocket in the center lined by electronegative carbonyl oxygens to be the site of interaction with a cation. G-quartet structures exhibit some specific behaviors as nucleic acids (Williamson, 1994; Rhodes, et al., 1995; Gilber et al., 1999). They are very polymorphic. A family of related G-quartet structures, such as a single-stranded monomer, hairpin dimmers and parallel stranded tetramers, can be formed based upon sequence, concentration and base composition of the nucleic acids. Also, they can readily discriminate between different monovalent cations. G-tetrad forming oligonucleotides have specific affinity for monovalent cations and G-quartet formation strongly depends on the presence of cations. The order of preference that has been proposed is $K^+>Rb^+>Na^+>Li^+$ or $Cs^+$ (Sen et al., 1990; Jing et al., 1997). The selectivity of G-quartet structures for cations is due to the ionic radius, and potassium appears to have the optimal size to interact within a G-octamer. The folding and unfolding transitions for G-quartet structures are extremely slow, so that the G-quartet structures are both thermodynamically and kinetically stable. The stability and slow kinetic transition of G-quartet structures have some important consequences for their biological rules.

Several groups have demonstrated that G-rich oligonucleotides forming G-quartet structures can be potential therapeutic drugs, such as potent HIV inhibitors (Jing et al., 2000; Jing et al., 1998; Jing et al., 2000b) and inhibitor of human nuclear top 1. The previous studies demonstrated that the G-rich oligonucleotides form a stable intramolecular G-quartet structure to inhibit HIV-1 integrase by binding it into the active site of the target protein (Katchalski-Katzri et al., 1992; Vakser et al., 1996).

The delivery of G-quartet oligonucleotides to the designed targets is a critical issue for oligonucleotides as pharmaceuticals. To utilize this structure as a pharmaceutical, it is imperative that the G-quartet oligonucleotides be delivered into the nuclei of target cells. The present invention is the first to deliver these G-quartet oligonucleotides into the nuclei of the target cells.

BRIEF SUMMARY OF THE INVENTION

The present invention is drawn to methods to deliver G-rich oligonucleotides into a cell and specifically into the nucleus of the cell. The novel intracellular delivery system of the present invention is based upon the property of potassium-induced formation of the G-quartet structure. It is also contemplated that the G-rich oligonucleotides may be used as therapeutic agents to treat viral infections or viral diseases or hyperproliferative diseases, such as cancer. The G-rich oligonucleotides are designed to inhibit the function of target proteins through binding interaction, which is different from antisense oligonucleotides that act as a template through hybridization to target a specific mRNA or DNA to inhibit gene expression at the level of transcription or translation.

A specific embodiment of the present invention is a method of intracellular delivery of a G-rich oligonucleotide comprising the steps of denaturing the oligonucleotide; mixing the oligonucleotide with a lipid to form an oligonucleotide-lipid complex; and incubating the oligonucleotide-lipid complex with a cell, wherein the oligonucleotide is internalized into the cell. In specific embodiments, the internalized oligonucleotide is induced to form a G-quartet structure.

In a further embodiment, the G-quartet structure enters the nucleus. The G-quartet structure inhibits HIV integrase. More specifically, the G-quartet is SEQ. ID. NO. 1 or SEQ. ID. NO. 2.

Yet further, the G-quartet may inhibit binding of transcription factors, for example, but not limited to STAT and NFκB. In specific embodiments, the G-quartet structure inhibits STAT, for example, the G-quartet is SEQ. ID. NO. 1, SEQ. ID. NO. 2 or SEQ. ID. NO. 3.

Another embodiment of the present invention is a method of inhibiting hyperproliferative cell growth comprising administering to the cell an effective amount of a G-rich oligonucleotide composition, wherein the composition modulates a protein involved in cell proliferation thereby inhibiting hyperproliferative cell growth. Specifically, the protein is a STAT protein, for example, STAT1, STAT2, STAT3, STAT4, STAT5a, STAT5b or STAT6. In addition to the G-rich oligonucleotide composition, an antitumor agent may be administered in combination to the cell. The antitumor agent is a chemotherapeutic drug.

In specific embodiments, the hyperproliferative cell is a tumor cell. For example, the tumor cell is a melanoma cell, a bladder cancer cell, a breast cancer cell, a lung cancer cell, a colon cancer cell, a prostate cancer cell, a liver cancer cell, a pancreatic cancer cell, a stomach cancer cell, a testicular cancer cell, a brain cancer cell, an ovarian cancer cell, a lymphatic cancer cell, a skin cancer cell, a brain cancer cell, a bone cancer cell, or a soft tissue cancer cell.

Another embodiment of the present invention is a method of treating a hyperproliferative disease comprising administering to a patient an effective amount of a G-rich oligonucleotide in an amount effective to treat the hyperproliferative disease. Yet further, the G-rich composition may be administered in combination with chemotherapy, immunotherapy, surgery, or radiotherapy. The composition comprises a lipid-oligonucleotide complex. The patient is a human.

In specific embodiments, the hyperproliferative disease is cancer. For example, the cancer is selected from the group consisting of melanoma, bladder, non-small cell lung, small cell lung, lung, hepatocarcinoma, retinoblastoma, astrocytoma, glioblastoma, neuroblastoma, head, neck, breast, pancreatic, gum, tongue, prostate, renal, bone, testicular, ovarian, mesothelioma, cervical, gastrointestinal lymphoma, brain, and colon cancer.

In further embodiments, the hyperproliferative disease is selected from the group consisting of rheumatoid arthritis, inflammatory bowel disease, osteoarthritis, leiomyomas, adenomas, lipomas, hemangiomas, fibromas, vascular occlusion, restenosis, atherosclerosis, pre-neoplastic lesions (such as adenomatous hyperplasia and prostatic intraepithelial neoplasia), carcinoma in situ, oral hairy leukoplakia, and psoriasis.

Other embodiments of the present invention included an isolated oligonucleotide comprising the sequence of SEQ. ID. NO. 1, SEQ. ID. NO. 2 or SEQ. ID. NO. 3. It is envisioned that SEQ. ID. NO. 1, SEQ. ID. NO. 2 or SEQ. ID. NO. 3 is an anti-viral agent or an anti-cancer agent.

A further embodiment is a method of treating a viral infection comprising administering to a patient an effective amount of a composition comprising SEQ. ID. NO. 1, wherein the amount of the composition inhibits viral activity. The composition comprises a lipid-oligonucleotide complex. More specifically, the viral infection is HIV.

Another embodiment is a method of treating a viral infection comprising administering to a patient an effective amount of a composition comprising SEQ. ID. NO. 2, wherein the amount of the composition inhibits viral activity. The composition comprises a lipid-oligonucleotide complex. More specifically, the viral infection is HIV.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings.

FIG. 1A shows the structure models of G-quartets, T30923 (SEQ. ID. NO. 1), T40214 (SEQ. ID. NO. 2) and T40216 (SEQ. ID. NO. 3). FIG. 1B shows a CD spectra of T30923 (SEQ. ID. NO. 1), T40214 (SEQ. ID. NO. 2), T40216 (SEQ. ID. NO. 3) and ns-ODN.

FIG. 4A shows T30923 (SEQ. ID. NO. 1) in G-quartet structure mixed with Lipofectin at ratio of oligo/lipid from 1:0 to 1:10, (FIG. 4B) and (FIG. 4C) T30923 (SEQ. ID. NO. 1) and T40214 (SEQ. ID. NO. 2) in denatured state incorporated with Lipofectin at ratio of oligo/lipid from 1:0 to 1:20, respectively.

FIG. 7A shows T40214 (SEQ. ID. NO. 2) delivered into 3T3 cells. FIG. 7B shows T30923 (SEQ. ID. NO. 1) delivered into 3T3 cells.

FIG. 7C shows T40214 delivered into CEMSS cells. FIG. 7D shows T30923 (SEQ. ID. NO. 1) delivered into CEMSS cells. FIG. 7E shows T40214 (SEQ. ID. NO. 2) delivered into MT4 cells. FIG. 7F shows T30923 (SEQ. ID. NO. 1) delivered into MT4 cells. FIG. 7G shows T40214/G-quartet (SEQ. ID. NO. 2). FIG. 7H shows T30923/G-quartet (SEQ. ID. NO. 1).

FIG. 11B shows the percentage of inhibition of STAT3 and STAT1 vs. drug concentration.

FIG. 12A shows the top view of the complex. The G-quartets (white wires) interact with a STAT 3 dimer binding to the DNA. FIG. 12B shows the front view of the complex.

FIG. 13A shows that T40214 (SEQ. ID. NO. 2) was incorporated with PEI at ratio of oligo/lipid from 1:0 to 1:20. FIG. 13B shows a plot obtained based upon the analysis of all the intensities of the bands in each lane of the gel, showing the efficiency of formation of lipid-DNA complexes vs. the ratio of lipid/DNA. FIG. 13C shows that the molecules of DNA oligonucleotides were delivered inside cells by lipid-DNA complexes.

ID. NO. 2), T40216 (SEQ. ID. NO. 3) and ns-ODN. FIG. 14A shows the inhibition of DNA-binding activity of STAT3. FIG. 14B and FIG. 14C show the concentration-dependent inhibition of DNA-binding activity of STAT3.

DETAILED DESCRIPTION OF THE INVENTION

Figure 1:
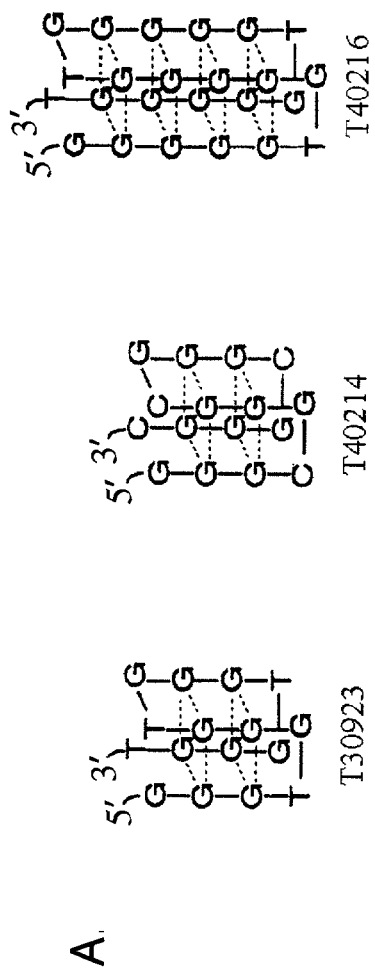
FIG. 1A and FIG. 1B show the G-quartet models.
Figure 1:
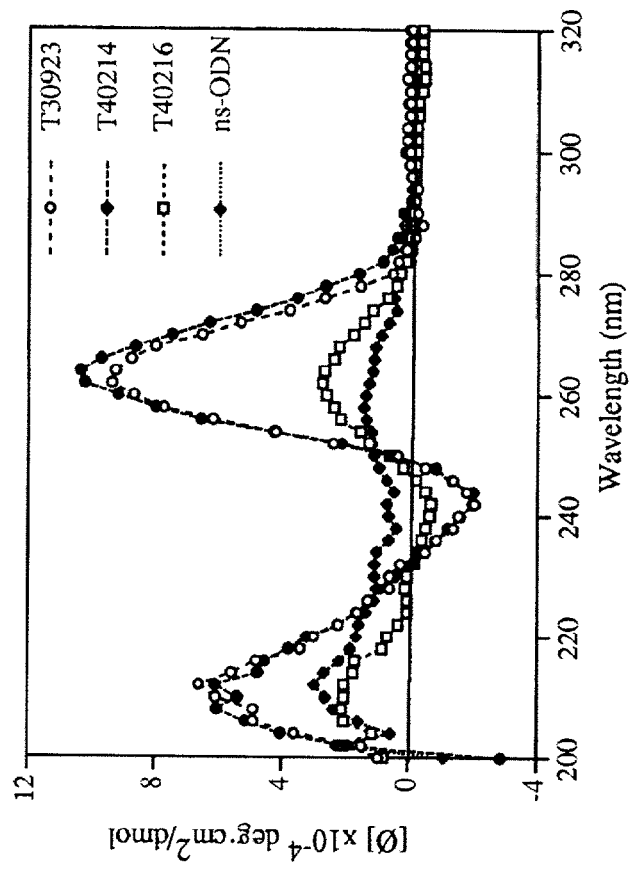
Figure 2:
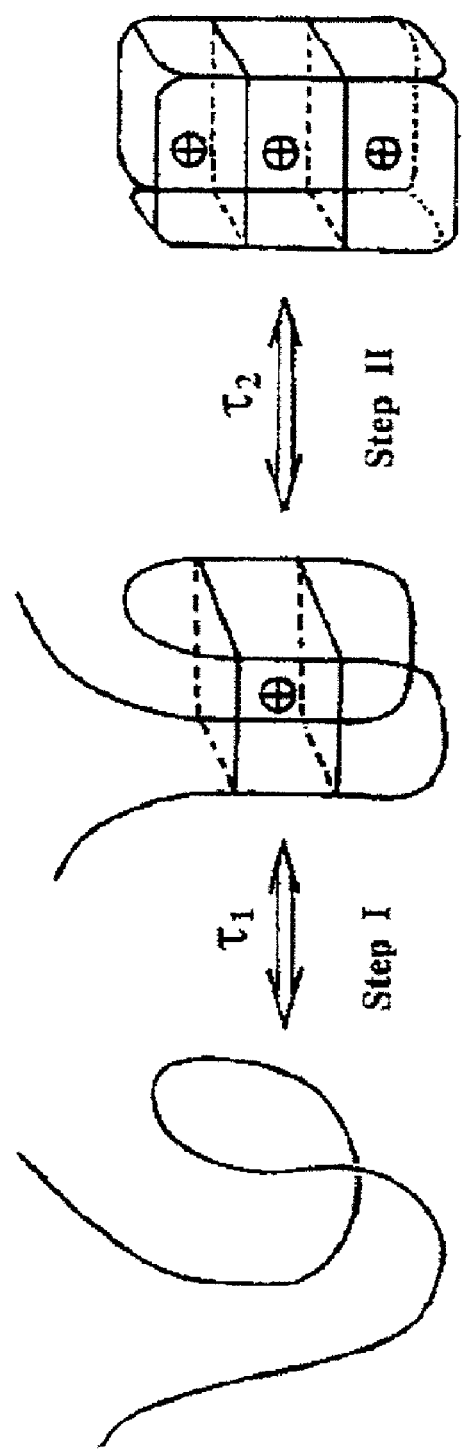
FIG. 2 shows the two-step kinetic model of $K^+$-induced folding of G-quartet oligonucleotides, which has been identified previously by NMR and UV kinetics.

It is readily apparent to one skilled in the art that various embodiments and modifications can be made to the invention disclosed in this Application without departing from the scope and spirit of the invention.

The following terms as defined will be used in the description of the invention.

As used herein, the use of the word "a" or "an" when used in conjunction with the term "comprising" in the sentences and/or the specification may mean "one," but it is also consistent with the meaning of "one or more," "at least one," and "one or more than one."

The term "base" as used herein includes both the deoxyribonucleic acids and ribonucleic acids. The following abbreviations are used. "A" refers to adenine as well as to its deoxyribose derivative, "T" refers to thymine, "U" refers to uridine, "G" refers to guanine as well as its deoxyribose derivative, "C" refers to cytosine as well as its deoxyribose derivative. A person having ordinary skill would readily recognize that these bases may be modified or derivatized to optimize the methods of the present invention. In addition, bases can refer to unnatural (synthetic) bases used in place of an A, C, T, or G.

As used herein the term "effective amount" is defined as an amount of the agent (such as the oligonucleotide or a combination of the oligonucleotide and an other agent) that is sufficient to detectably ameliorate, reduce, minimize or limit the extent of the disease or its symptoms. In certain highly preferred embodiments, it also includes elimination, eradication or cure of disease.

The term "cancer" as used herein is defined as a hyperproliferation of cells whose unique trait—loss of normal controls—results in unregulated growth, lack of differentiation, local tissue invasion, and metastasis. Examples include but are not limited to, breast cancer, prostate cancer, ovarian cancer, cervical cancer, skin cancer, pancreatic cancer, colorectal cancer, renal cancer and lung cancer.

The term "hyperproliferative disease" is defined as a disease that results from a hyperproliferation of cells. Exemplary hyperproliferative diseases include, but are not limited to cancer or autoimmune diseases. Other hyperproliferative diseases may include vascular occlusion, restenosis, atherosclerosis, or inflammatory bowel disease.

The term "oligonucleotide" as used herein is defined as a molecule comprised of two or more deoxyribonucleotides or ribonucleotides, preferably more than ten. Its exact size will depend on many factors including the specificity and antiviral activity of the oligonucleotide for various viruses. In addition, bases can refer to unnatural (synthetic) bases used in place of an A, C, T or G.

The term "pathophysiological state" as used herein refers to any abnormal undesirable or life-threatening condition caused directly or indirectly by a virus.

A. Oligonucleotides

Generally, the oligonucleotides of the present invention contain a percentage of guanosine bases. The guanosine is important in forming tetrads which stabilize the three dimensional structure of the oligonucleotides. Thus, the oligonucleotides of the present invention may have any percentage of guanosine bases which will allow for tetrad formation. Preferably, the oligonucleotides of the present invention contain two or more segments of two or more guanosine bases, and an overall high percentage of G in order to enable the oligonucleotide to form at least one guanosine tetrad.

In specific embodiments, the oligonucleotides include, but are not limited to the following sequences T30923: GGGTGGGTGGGTGGGT (SEQ. ID. NO. 1); T40214: GGGCGGGCGGGCGGGC (SEQ. ID. NO. 2); T40216: GGGGGTGGGGGTGGGGGTGGGGGT (SEQ. ID. NO. 3).

B. Lipid Compositions

In certain embodiments, the present invention concerns a novel G-rich oligonucleotide composition comprising one or more lipids associated with the present invention. A G-rich oligonucleotide associated with a lipid may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure. A lipid or lipid/G-rich oligonucleotide associated composition of the present invention is not limited to any particular structure. For example, they may also simply be interspersed in a solution, possibly forming aggregates which are not uniform in either size or shape. In another example, they may be present in a bilayer structure, as micelles, or with a "collapsed" structure. In another non-limiting example, a lipofectamine(Gibco BRL)-G-rich oligonucleotide or Superfect (Qiagen)-G-rich oligonucleotide complex is also contemplated.

In certain embodiments, a lipid component of a composition is uncharged or primarily uncharged. In one embodiment, a lipid component of a composition comprises one or more neutral lipids. In another aspect, a lipid component of a composition may be substantially free of anionic and cationic lipids, such as certain phospholipids (e.g., phosphatidyl choline) and cholesterol. In certain aspects, a lipid component of an uncharged or primarily uncharged lipid composition comprises about 95%, about 96%, about 97%, about 98%, about 99% or 100% lipids without a charge, substantially uncharged lipid(s), and/or a lipid mixture with equal numbers of positive and negative charges.

In a further embodiment, the lipid may be a charged. For example, charged phospholipids may be used for preparing a lipid composition according to the present invention and can carry a net positive charge or a net negative charge. In one embodiment, the charge lipid may be a "polycationic polymer", which as used herein is defined as a water-soluble positively charged compound. The polycationic polymer neutralizes the negative charge of the nucleic acids allowing close proximity of the nucleic acids to the negatively charge cell membrane. Exemplary polycationic polymers include but are not limited to, polylysine, polyethyleneimine, polyhistidine, protamine, polyvinylamines, polyvinylpyridine, polymethacrylates, and polyornithine.

1. Emulsions

A lipid can be comprised in an emulsion. A lipid emulsion is a substantially permanent heterogenous liquid mixture of two or more liquids that do not normally dissolve in each other, by mechanical agitation or by small amounts of additional substances known as emulsifiers. Methods for preparing lipid emulsions and adding additional components are well known in the art (e.g., Modern Pharmaceutics, 1990, incorporated herein by reference).

For example, one or more lipids are added to ethanol or chloroform or any other suitable organic solvent and agitated by hand or mechanical techniques. The solvent is then evaporated from the mixture leaving a dried glaze of lipid. The lipids are resuspended in aqueous media, such as phosphate buffered saline, resulting in an emulsion. To achieve a more homogeneous size distribution of the emulsified lipids, the mixture may be sonicated using conventional sonication techniques, further emulsified using microfluidization (using, for example, a Microfluidizer, Newton, Mass.), and/or extruded under high pressure (such as, for example, 600 psi) using an Extruder Device (Lipex Biomembranes, Vancouver, Canada).

2. Micelles

A lipid can be comprised in a micelle. A micelle is a cluster or aggregate of lipid compounds, generally in the form of a lipid monolayer, and may be prepared using any micelle producing protocol known to those of skill in the art (e.g., Canfield et al., 1990; El-Gorab et al., 1973, each incorporated herein by reference). For example, one or more lipids are typically made into a suspension in an organic solvent, the solvent is evaporated, the lipid is resuspended in an aqueous medium, sonicated and then centrifuged.

3. Liposomes

In particular embodiments, a lipid comprises a liposome. A "liposome" is a generic term encompassing a variety of single and multilamellar lipid vehicles formed by the generation of enclosed lipid bilayers or aggregates. Liposomes may be characterized as having vesicular structures with a bilayer membrane, generally comprising a phospholipid, and an inner medium that generally comprises an aqueous composition.

A multilamellar liposome has multiple lipid layers separated by aqueous medium. They form spontaneously when lipids comprising phospholipids are suspended in an excess of aqueous solution. The lipid components undergo self-rearrangement before the formation of closed structures and entrap water and dissolved solutes between the lipid bilayers (Ghosh and Bachhawat, 1991). Lipophilic molecules or molecules with lipophilic regions may also dissolve in or associate with the lipid bilayer.

In particular embodiments, a lipid and/or G-rich oligonucleotides may be, for example, encapsulated in the aqueous interior of a liposome, interspersed within the lipid bilayer of a liposome, attached to a liposome via a linking molecule that is associated with both the liposome and the G-rich oligonucleotides, entrapped in a liposome, complexed with a liposome, etc.

A liposome used according to the present invention can be made by different methods, as would be known to one of ordinary skill in the art. Phospholipids can form a variety of structures other than liposomes when dispersed in water, depending on the molar ratio of lipid to water. At low ratios the liposome is the preferred structure.

For example, a phospholipid (Avanti Polar Lipids, Alabaster, AL), such as for example the neutral phospholipid dioleoylphosphatidylcholine (DOPC), is dissolved in tert-butanol. The lipid(s) is then mixed with the G-rich oligonucleotides, and/or other component(s). Tween 20 is added to the lipid mixture such that Tween 20 is about 5% of the composition's weight. Excess tert-butanol is added to this mixture such that the volume of tert-butanol is at least 95%. The mixture is vortexed, frozen in a dry ice/acetone bath and lyophilized overnight. The lyophilized preparation is stored at −20° C. and can be used up to three months. When required the lyophilized liposomes are reconstituted in 0.9% saline. The average diameter of the particles obtained using Tween 20 for encapsulating the G-rich oligonucleotide is about 0.7 to about 1.0 μm in diameter.

Alternatively, a liposome can be prepared by mixing lipids in a solvent in a container, e.g., a glass, pear-shaped flask. The container should have a volume ten-times greater than the volume of the expected suspension of liposomes. Using a rotary evaporator, the solvent is removed at approximately 40° C. under negative pressure. The solvent normally is removed within about 5 min. to 2 hours, depending on the desired volume of the liposomes. The composition can be dried further in a desiccator under vacuum. The dried lipids generally are discarded after about 1 week because of a tendency to deteriorate with time.

Dried lipids can be hydrated at approximately 25–50 mM phospholipid in sterile, pyrogen-free water by shaking until all the lipid film is resuspended. The aqueous liposomes can be then separated into aliquots, each placed in a vial, lyophilized and sealed under vacuum.

In other alternative methods, liposomes can be prepared in accordance with other known laboratory procedures (e.g., see Bangham et al., 1965; Gregoriadis, 1979; Deamer and Uster 1983, Szoka and Papahadjopoulos, 1978, each incorporated herein by reference in relevant part). These methods differ in their respective abilities to entrap aqueous material and their respective aqueous space-to-lipid ratios.

The dried lipids or lyophilized liposomes prepared as described above may be dehydrated and reconstituted in a solution of inhibitory peptide and diluted to an appropriate concentration with an suitable solvent, e.g., DPBS. The mixture is then vigorously shaken in a vortex mixer. Unencapsulated additional materials, such as agents including but not limited to hormones, drugs, nucleic acid constructs and the like, are removed by centrifugation at 29,000×g and the liposomal pellets washed. The washed liposomes are resuspended at an appropriate total phospholipid concentration, e.g., about 50–200 mM. The amount of additional material or active agent encapsulated can be determined in accordance with standard methods. After determination of the amount of additional material or active agent encapsulated in the liposome preparation, the liposomes may be diluted to appropriate concentrations and stored at 4° C. until use. A pharmaceutical composition comprising the liposomes will usually include a sterile, pharmaceutically acceptable carrier or diluent, such as water or saline solution.

The size of a liposome varies depending on the method of synthesis. Liposomes in the present invention can be a variety of sizes. In certain embodiments, the liposomes are small, e.g., less than about 100 nm, about 90 nm, about 80 nm, about 70 nm, about 60 nm, or less than about 50 nm in external diameter. In preparing such liposomes, any protocol described herein, or as would be known to one of ordinary skill in the art may be used. Additional non-limiting examples of preparing liposomes are described in U.S. Pat. Nos. 4,728,578, 4,728,575, 4,737,323, 4,533,254, 4,162,282, 4,310,505, and 4,921,706; International Applications PCT/US85/01161 and PCT/US89/05040; U.K. Patent Application GB 2193095 A; and Liposome Technology, 1984, each incorporated herein by reference).

A liposome suspended in an aqueous solution is generally in the shape of a spherical vesicle, having one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and without the liposome, the lipid molecules may form a bilayer, known as a lamella, of the arrangement XY-YX. Aggregates of lipids may form when the hydrophilic and hydrophobic parts of more than one lipid molecule become associated with each other. The size and shape of these aggregates will depend upon many different variables, such as the nature of the solvent and the presence of other compounds in the solution.

The production of lipid formulations often is accomplished by sonication or serial extrusion of liposomal mixtures after (I) reverse phase evaporation (II) dehydration-rehydration (III) detergent dialysis and (IV) thin film hydration. In one aspect, a contemplated method for preparing liposomes in certain embodiments is heating sonicating, and sequential extrusion of the lipids through filters or membranes of decreasing pore size, thereby resulting in the formation of small, stable liposome structures. This preparation produces liposomal/G-rich oligonucleotides or liposomes only of appropriate and uniform size, which are structurally stable and produce maximal activity. Such techniques are well-known to those of skill in the art (see, for example Martin, 1990).

Once manufactured, lipid structures can be used to encapsulate compounds that are toxic (e.g., chemotherapeutics) or labile (e.g., nucleic acids) when in circulation. The physical characteristics of liposomes depend on pH, ionic strength and/or the presence of divalent cations. Liposomes can show low permeability to ionic and/or polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and/or results in an increase in permeability to ions, sugars and/or drugs. Liposomal encapsulation has resulted in a lower toxicity and a longer serum half-life for such compounds (Gabizon et al., 1990).

Liposomes interact with cells to deliver agents via four different mechanisms: Endocytosis by phagocytic cells of the reticuloendothelial system such as macrophages and/or neutrophils; adsorption to the cell surface, either by non-specific weak hydrophobic and/or electrostatic forces, and/or by specific interactions with cell-surface components; fusion with the plasma cell membrane by insertion of the lipid bilayer of the liposome into the plasma membrane, with simultaneous release of liposomal contents into the cytoplasm; and/or by transfer of liposomal lipids to cellular and/or subcellular membranes, and/or vice versa, without any association of the liposome contents. Varying the liposome formulation can alter which mechanism is operative, although more than one may operate at the same time.

Numerous disease treatments are using lipid based gene transfer strategies to enhance conventional or establish novel therapies, in particular therapies for treating hyperproliferative diseases. Advances in liposome formulations have improved the efficiency of gene transfer in vivo (Templeton et al., 1997) and it is contemplated that liposomes are prepared by these methods. Alternate methods of preparing lipid-based formulations for nucleic acid delivery are described (WO 99/18933).

In another liposome formulation, an amphipathic vehicle called a solvent dilution microcarrier (SDMC) enables integration of particular molecules into the bi-layer of the lipid vehicle (U.S. Pat. No. 5,879,703). The SDMCs can be used to deliver lipopolysaccharides, polypeptides, nucleic acids and the like. Of course, any other methods of liposome preparation can be used by the skilled artisan to obtain a desired liposome formulation in the present invention.

C. Liposome Targeting

Association of the G-rich oligonucleotide with a liposome can improve biodistribution and other properties of the G-rich oligonucleotide. For example, liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980). Successful liposome-mediated gene transfer in rats after intravenous injection has also been accomplished (Nicolau et al., 1987).

It is contemplated that a liposome/G-rich oligonucleotide composition can comprise additional materials for delivery to a tissue. For example, in certain embodiments of the invention, the lipid or liposome may be associated with a hemagglutinating virus (HVJ). This has been shown to facilitate fusion with the cell membrane and promote cell entry of liposome-encapsulated DNA (Kaneda et al., 1989). In another example, the lipid or liposome may be complexed or employed in conjunction with nuclear non-histone chromosomal proteins (HMG-1) (Kato et al., 1991). In yet further embodiments, the lipid may be complexed or employed in conjunction with both HVJ and HMG-1.

Targeted delivery is achieved by the addition of ligands without compromising the ability of these liposomes deliver large amounts of G-rich oligonucleotides. It is contemplated that this will enable delivery to specific cells, tissues and organs. The targeting specificity of the ligand-based delivery systems are based on the distribution of the ligand receptors on different cell types. The targeting ligand may either be non-covalently or covalently associated with the lipid complex, and can be conjugated to the liposomes by a variety of methods.

1. Cross-Linkers

Bifunctional cross-linking reagents have been extensively used for a variety of purposes including preparation of affinity matrices, modification and stabilization of diverse structures, identification of ligand and receptor binding sites, and structural studies. Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino, sulfhydryl, guanidino, indole, carboxyl specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

Exemplary methods for cross-linking ligands to liposomes are described in U.S. Pat. No. 5,603,872 and U.S. Pat. No. 5,401,511, each specifically incorporated herein by reference in its entirety). Various ligands can be covalently bound to liposomal surfaces through the cross-linking of amine residues. Liposomes, in particular, multilamellar vesicles (MLV) or unilamellar vesicles such as microemulsified liposomes (MEL) and large unilamellar liposomes (LUVET), each containing phosphatidylethanolamine (PE), have been prepared by established procedures. The inclusion of PE in the liposome provides an active functional residue, a primary amine, on the liposomal surface for cross-linking purposes. Ligands such as epidermal growth factor (EGF) have been successfully linked with PE-liposomes. Ligands are bound covalently to discrete sites on the liposome surfaces. The number and surface density of these sites will be dictated by the liposome formulation and the liposome type. The liposomal surfaces may also have sites for non-covalent association. To form covalent conjugates of ligands and liposomes, cross-linking reagents have been studied for effectiveness and biocompatibility. Cross-linking reagents include glutaraldehyde (GAD), bifunctional oxirane (OXR), ethylene glycol diglycidyl ether (EGDE), and a water soluble carbodiimide, preferably 1-ethyl-3-(3-dimethylaminopropyl) carbodiimide (EDC). Through the complex chemistry of cross-linking, linkage of the amine residues of the recognizing substance and liposomes is established.

In another example, heterobifunctional cross-linking reagents and methods of using the cross-linking reagents are described (U.S. Pat. No. 5,889,155, specifically incorporated herein by reference in its entirety). The cross-linking reagents combine a nucleophilic hydrazide residue with an electrophilic maleimide residue, allowing coupling in one example, of aldehydes to free thiols. The cross-linking reagent can be modified to cross-link various functional groups and is thus useful for cross-linking polypeptides and sugars.

2. Targeting Ligands

The targeting ligand can be either anchored in the hydrophobic portion of the complex or attached to reactive terminal groups of the hydrophilic portion of the complex. The targeting ligand can be attached to the liposome via a linkage to a reactive group, e.g., on the distal end of the hydrophilic polymer. Preferred reactive groups include amino groups, carboxylic groups, hydrazide groups, and thiol groups. The coupling of the targeting ligand to the hydrophilic polymer can be performed by standard methods of organic chemistry that are known to those skilled in the art. In certain embodiments, the total concentration of the targeting ligand can be from about 0.01 to about 10% mol.

Targeting ligands are any ligand specific for a characteristic component of the targeted region. Preferred targeting ligands include proteins such as polyclonal or monoclonal antibodies, antibody fragments, or chimeric antibodies, enzymes, or hormones, or sugars such as mono-, oligo- and poly-saccharides (see, Heath et al., Chem. Phys. Lipids 40:347 (1986)) For example, disialoganglioside GD2 is a tumor antigen that has been identified neuroectodermal origin tumors, such as neuroblastoma, melanoma, small-cell lung carcenoma, glioma and certain sarcomas (Mujoo et al., 1986). Liposomes containing anti-disialoganglioside GD2 monoclonal antibodies have been used to aid the targeting of the liposomes to cells expressing the tumor antigen (Pagnan et al., 1999). In another non-limiting example, breast and gynecological cancer antigen specific antibodies are described in U.S. Pat. No. 5,939,277, incorporated herein by reference. In a further non-limiting example, prostate cancer specific antibodies are disclosed in U.S. Pat. No. 6,107,090, incorporated herein by reference. Thus, it is contemplated that the antibodies described herein or as would be known to one of ordinary skill in the art may be used to target specific tissues and cell types in combination with the compositions and methods of the present invention. In certain embodiments of the invention, contemplated targeting ligands interact with integrins, proteoglycans, glycoproteins, receptors or transporters. Suitable ligands include any that are specific for cells of the target organ, or for structures of the target organ exposed to the circulation as a result of local pathology, such as tumors.

In certain embodiments of the present invention, in order to enhance the transduction of cells, to increase transduction of target cells, or to limit transduction of undesired cells, antibody or cyclic peptide targeting moieties (ligands) are associated with the lipid complex. Such methods are known in the art. For example, liposomes have been described further that specifically target cells of the mammalian central nervous system (U.S. Pat. No. 5,786,214, incorporated herein by reference). The liposomes are composed essentially of N-glutarylphosphatidylethanolamine, cholesterol and oleic acid, wherein a monoclonal antibody specific for neuroglia is conjugated to the liposomes. It is contemplated that a monoclonal antibody or antibody fragment may be used to target delivery to specific cells, tissues, or organs in the animal, such as for example, brain, heart, lung, liver, etc.

Still further, a G-rich oligonucleotide can be delivered to a target cell via receptor-mediated delivery and/or targeting vehicles comprising a lipid or liposome. These take advantage of the selective uptake of macromolecules by receptor-mediated endocytosis that will be occurring in a target cell. In view of the cell type-specific distribution of various receptors, this delivery method adds another degree of specificity to the present invention.

Thus, in certain aspects of the present invention, a ligand will be chosen to correspond to a receptor specifically expressed on the target cell population. A cell-specific G-rich oligonucleotide delivery and/or targeting vehicle can comprise a specific binding ligand in combination with a liposome. The G-rich oligonucleotides to be delivered are housed within a liposome and the specific binding ligand is functionally incorporated into a liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In certain embodiments, a receptor-mediated delivery and/or targeting vehicles comprise a cell receptor-specific ligand and a G-rich oligonucleotide-binding agent. Others comprise a cell receptor-specific ligand to which G-rich oligonucleotides to be delivered has been operatively attached. For example, several ligands have been used for receptor-mediated gene transfer (Wu and Wu, 1987; Wagner et al., 1990; Perales et al., 1994; Myers, EPO 0273085), which establishes the operability of the technique. In another example, specific delivery in the context of another mammalian cell type has been described (Wu and Wu, 1993; incorporated herein by reference).

In still further embodiments, the specific binding ligand may comprise one or more lipids or glycoproteins that direct cell-specific binding. For example, lactosyl-ceramide, a galactose-terminal asialganglioside, have been incorporated into liposomes and observed an increase in the uptake of the insulin gene by hepatocytes (Nicolau et al., 1987). The asialoglycoprotein, asialofetuin, which contains terminal galactosyl residues, also has been demonstrated to target liposomes to the liver (Spanjer and Scherphof, 1983; Hara et al., 1996). The sugars mannosyl, fucosyl or N-acetyl glucosamine, when coupled to the backbone of a polypeptide, bind the high affinity manose receptor (U.S. Pat. No. 5,432, 260, specifically incorporated herein by reference in its entirety). It is contemplated that the cell or tissue-specific transforming constructs of the present invention can be specifically delivered into a target cell or tissue in a similar manner.

In another example, lactosyl ceramide, and peptides that target the LDL receptor related proteins, such as apolipoprotein E3 ("Apo E") have been useful in targeting liposomes to the liver (Spanjer and Scherphof, 1983; WO 98/0748).

Folate and the folate receptor have also been described as useful for cellular targeting (U.S. Pat. No. 5,871,727). In this example, the vitamin folate is coupled to the complex. The folate receptor has high affinity for its ligand and is overexpressed on the surface of several malignant cell lines, including lung, breast and brain tumors. Anti-folate such as methotrexate may also be used as targeting ligands. Transferrin mediated delivery systems target a wide range of replicating cells that express the transferrin receptor.

D. Lipid Administration

The actual dosage amount of a lipid composition (e.g., a liposome-G-rich oligonucleotide) administered to a patient can be determined by physical and physiological factors such as body weight, severity of condition, idiopathy of the patient and on the route of administration. With these considerations in mind, the dosage of a lipid composition for a particular subject and/or course of treatment can readily be determined.

The present invention can be administered intravenously, intradermally, intraarterially, intraperitoneally, intralesionally, intracranially, intraarticularly, intraprostaticaly, intrapleurally, intratracheally, intranasally, intravitreally, intravaginally, rectally, topically, intratumorally, intramuscularly, intraperitoneally, subcutaneously, intravesicularlly, mucosally, intrapericardially, orally, topically, locally and/or using aerosol, injection, infusion, continuous infusion, localized perfusion bathing target cells directly or via a catheter and/or lavage.

E. Intracellular Delivery System

A G-rich oligonucleotide, such as T30923, forms a stable and symmetric intramolecular G-quartet structure with about 15 Å width and 15 Å length in the presence of $K^+$ ions (Jing and Hogan, 1998). This structure seems to resemble a cylinder with positive charges inside and negative charges on the surface. The net charge on complex is most likely to be close to a neutral zwitterion under physiologic conditions.

The present invention provides a method of intracellular delivery of a G-rich oligonucleotide. The method comprises denaturing the oligonucleotide; mixing the oligonucleotide with a lipid to form an oligonucleotide-lipid complex; and incubating the oligonucleotide-lipid complex with a cell, wherein the oligonucleotide is internalized into the cell.

It is contemplated that the oligonucleotide is mixed with a lipid to form a lipid-oligo or lipid-DNA complex. One of skill in the art is aware that oligonucleotide and DNA are interchangeable. The lengthy discussion of lipid compositions, lipid administration employed therein is incorporated into this section by reference.

In the present invention, the delivery system is based upon the property of potassium dependent formation of G-quartet structure. The difference of $K^+$ concentrations inside and outside cells are used to induce the molecules of G-rich oligonucleotides forming different structures inside and outside cells. It is well known and understood by those of skill in the art that the $K^+$ ion concentration is 4 mM outside cells and 140 mM inside cells. Thus, the G-quartet is designed to stay in an unfolded structure in 4 mM $K^+$ and to fold in an environment containing 140 mM $K^+$.

According to the present invention, intracellular delivery of G-quartet oligonucleotides by DNA-lipid complexes can be divided into three steps: (1) binding and internalization of DNA by the cells, (2) escape of the DNA into the cytoplasm, and (3) entry of the DNA oligos into the nucleus. The primary driving force for the binding of the lipid-DNA complex to the cell membrane is electrostatic (Maurer et al., 1999; Chesnoy and Huang, 2000).

It is contemplated that the internalization of the lipid-DNA occurs mainly through endocytosis. The release of DNA oligonucleotides into the cytoplasm is most likely caused by the interaction between the cationic lipid and anionic molecules presented in the membrane. Thus, variation of the charge ratio, incubation time or the component of lipids can increase the percentage and speed of DNA oligonucleotides released from lipid-DNA complexes.

Yet further, the G-quartet oligonucleotides of the present invention enter the nucleus of the cell. The main reason that the refolded G-quartet molecules can penetrate into nucleus is considered to be due to their structural characters. After the oligonucleotide molecules are released from lipid-DNA complexes and enter the cytoplasm, they refold to form G-quartet structures due to the influence of $K^+$ ions inside the cells. The highly stable and compact G-quartet structure greatly enhances the ability of the oligonucleotides to resist nuclease digestion (Jing, 2000). Thus, the reformed G-quartet structure has a greater capacity to penetrate into the nucleus through the nuclear pores.

F. Treatment of Viral Infections

The present invention provides methods and compositions for treating a pathophysiological state caused by a virus, comprising the step of administering a an effective amount of an oligonucleotide, the amount being sufficient to inhibit the replication of the virus, wherein the oligonucleotide contains sufficient contiguous guanosines so that a guanosine tetrad (inter- or intra-molecular) can form, and the three dimensional structure of the oligonucleotide is stabilized by guanosine tetrads formed at strategic locations. Generally, this method of treating a virus-induced pathophysiological state may be useful against any virus. More preferably, the methods of the present invention may be useful in treating pathophysiological states caused by viruses such as herpes simplex virus, human papilloma virus, Epstein Barr virus, human immunodeficiency virus, adenovirus, respiratory syncytial virus, hepatitis B virus, human cytomegalovirus and HTLV I and II. In specific embodiments, the oligonucleotide inhibits HIV integrase, which is essential for HIV-1 replication.

Generally, the oligonucleotides of the present invention contain a percentage of guanosine bases high enough to ensure anti-viral efficacy. The guanosine is important in forming tetrads which stabilize the three dimensional structure of the oligonucleotides. Thus, the oligonucleotides of the present invention may have any percentage of guanosine bases which will allow for tetrad formation provided that the oligonucleotide exhibits anti-viral activity. Preferably, the oligonucleotides of the present invention contain two or more segments of two or more guanosine bases, and an overall high percentage of G in order to enable the oligonucleotide to form at least one guanosine tetrad.

G. Treatment of Hyperproliferative Diseases

In certain embodiments, a hyperproliferative disease may be treated by administering to a subject an effective amount of a G-rich oligonucleotide. The subject is preferably a mammal and more preferably a human.

The oligonucleotides of the present invention may have any percentage of guanosine bases which allow for tetrad formation provided that the oligonucleotide exhibits anti-cancer activity.

In the present invention, a hyperproliferative disease is further defined as cancer. In still further embodiments, the cancer is melanoma, non-small cell lung, small-cell lung, lung, leukemia, hepatocarcinoma, retinoblastoma, astrocytoma, glioblastoma, gum, tongue, neuroblastoma, head, neck, breast, pancreatic, prostate, renal, bone, testicular, ovarian, mesothelioma, cervical, gastrointestinal, lymphoma, brain, colon, sarcoma or bladder.

The cancer may include a tumor comprised of tumor cells. For example, tumor cells may include, but are not limited to melanoma cell, a bladder cancer cell, a breast cancer cell, a lung cancer cell, a colon cancer cell, a prostate cancer cell, a liver cancer cell, a pancreatic cancer cell, a stomach cancer cell, a testicular cancer cell, a brain cancer cell, an ovarian cancer cell, a lymphatic cancer cell, a skin cancer cell, a brain cancer cell, a bone cancer cell, or a soft tissue cancer cell.

In other embodiments, the hyperproliferative disease is rheumatoid arthritis, inflammatory bowel disease, osteoarthritis, leiomyomas, adenomas, lipomas, hemangiomas, fibromas, vascular occlusion, restenosis, atherosclerosis, pre-neoplastic lesions (such as adenomatous hyperplasia and prostatic intraepithelial neoplasia), carcinoma in situ, oral hairy leukoplakia, or psoriasis.

In a preferred embodiment of the present invention, G-rich oligonucleotides are administered in an effective amount to decrease, reduce, inhibit or abrogate the growth of a tumor. In specific embodiments of the present invention, G-rich oligonucleotides inhibit the DNA-binding activity of a signal transducer and activator of transcription (STAT) protein or nuclear factor kappa B (NFκB). The STAT protein is selected from the group consisting of STAT1, STAT2, STAT3, STAT4, STAT5a, STAT5b and STAT6. In specific embodiments, the G-rich oligonucleotide inhibits the DNA-binding activity of STAT-3.

Treatment regimens may vary as well, and often depend on tumor type, tumor location, disease progression, and health and age of the patient. Obviously, certain types of tumor will require more aggressive treatment, while at the same time, certain patients cannot tolerate more taxing protocols. The clinician will be best suited to make such decisions based on the known efficacy and toxicity (if any) of the therapeutic formulations.

Preferably, patients to be treated will have adequate bone marrow function (defined as a peripheral absolute granulocyte count of >2,000/mm$^3$ and a platelet count of 100,000/mm$^3$), adequate liver function (bilirubin <1.5 mg/dl) and adequate renal function (creatinine <1.5 mg/dl).

To kill cells, inhibit cell growth, decrease tumor or tissue size and otherwise reverse or reduce the malignant phenotype of tumor cells, using the methods and compositions of the present invention, one would generally contact a hyperproliferative cell with the G-rich oligonucleotide. The routes of administration will vary, naturally, with the location and nature of the lesion, and include, e.g., intradermal, transdermal, parenteral, intravenous, intramuscular, intranasal, subcutaneous, percutaneous, intratracheal, intraperitoneal, intratumoral, perfusion, lavage, direct injection, and oral administration and formulation.

In the case of surgical intervention, the present invention may be used preoperatively, to render an inoperable tumor subject to resection. Alternatively, the present invention may be used at the time of surgery, and/or thereafter, to treat residual or metastatic disease. For example, a resected tumor bed may be injected or perfused with a formulation comprising a G-rich oligonucleotide. The perfusion may be continued post-resection, for example, by leaving a catheter implanted at the site of the surgery. Periodic post-surgical treatment also is envisioned.

Continuous administration also may be applied where appropriate, for example, where a tumor is excised and the tumor bed is treated to eliminate residual, microscopic disease. Delivery via syringe or catherization is preferred. Such continuous perfusion may take place for a period from about 1–2 hours, to about 2–6 hours, to about 6–12 hours, to about 12–24 hours, to about 1–2 days, to about 1–2 wk or longer following the initiation of treatment. Generally, the dose of the therapeutic composition via continuous perfusion will be equivalent to that given by a single or multiple injections, adjusted over a period of time during which the perfusion occurs. It is further contemplated that limb perfusion may be used to administer therapeutic compositions of the present invention, particularly in the treatment of melanomas and sarcomas.

In certain embodiments, the tumor being treated may not, at least initially, be resectable. Treatments with therapeutic antibodies may increase the resectability of the tumor due to shrinkage at the margins or by elimination of certain particularly invasive portions. Following treatments, resection may be possible. Additional treatments subsequent to resection will serve to eliminate microscopic residual disease at the tumor site.

H. Combination Treatments

In order to increase the effectiveness of the G-rich oligonucleotides of the present invention, it may be desirable to combine the oligonucleotides of the present invention with other agents effective in the treatment of hyperproliferative disease, such as anti-cancer agents, or with surgery. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. Anti-cancer agents include biological agents (biotherapy), chemotherapy agents, and radiotherapy agents. More generally, these other compositions would be provided in a combined amount effective to kill or inhibit proliferation of the cell. This process may involve contacting the cells with the antibodies of the present invention and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the antibodies and the other includes the second agent(s).

Alternatively, the oligonucleotides of the present invention may precede or follow the other anti-cancer agent treatment by intervals ranging from minutes to weeks. In embodiments where the other anti-cancer agent and oligonucleotides are applied separately to the cell, one would generally ensure that a significant period of time did not expire between the time of each delivery, such that the agent and oligonucleotides would still be able to exert an advantageously combined effect on the cell. In such instances, it is contemplated that one may contact the cell with both modalities within about 12–24 h of each other and, more preferably, within about 6–12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

1. Chemotherapy

Cancer therapies also include a variety of chemical based treatments. Some examples of chemotherapeutic agents include antibiotic chemotherapeutics such as Doxorubicin, Daunorubicin, Adriamycin, Mitomycin (also known as mutamycin and/or mitomycin-C), Actinomycin D (Dactinomycin), Bleomycin, Plicomycin, plant alkaloids such as Taxol, Vincristine, Vinblastine, miscellaneous agents such as Cisplatin (CDDP), etoposide (VP16), Tumor Necrosis Factor, and alkylating agents such as, Carmustine, Melphalan (also known as alkeran, L-phenylalanine mustard, phenylalanine mustard, L-PAM, or L-sarcolysin, is a phenylalanine derivative of nitrogen mustard), Cyclophosphamide, Chlorambucil, Busulfan (also known as myleran), Lomustine.

Some examples of other agents include, but are not limited to, Carboplatin, Procarbazine, Mechlorethamine, Camptothecin, Ifosfamide, Nitrosurea, Etoposide (VP16), Tamoxifen, Raloxifene, Toremifene, Idoxifene, Droloxifene, TAT-59, Zindoxifene, Trioxifene, ICI 182,780, EM-800, Estrogen Receptor Binding Agents, Gemcitabien, Navelbine, Farnesyl-protein transferase inhibitors, Transplatinum, 5-Fluorouracil, hydrogen peroxide, and Methotrexate, Temazolomide (an aqueous form of DTIC), Mylotarg, Dolastatin-10, Bryostatin, or any analog or derivative variant of the foregoing.

2. Radiotherapeutic Agents

Radiotherapeutic agents and factors include radiation and waves that induce DNA damage for example, γ-irradiation, X-rays, UV-irradiation, microwaves, electronic emissions, radioisotopes, and the like. Therapy may be achieved by irradiating the localized tumor site with the above described forms of radiations. It is most likely that all of these factors effect a broad range of damage DNA, on the precursors of DNA, the replication and repair of DNA, and the assembly and maintenance of chromosomes.

Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

3. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

4. Gene Therapy

In yet another embodiment, gene therapy in conjunction with the combination therapy using the oligonucleotides compounds described in the invention are contemplated. A variety of genes that may be targeted for gene therapy of some form in combination with the present invention include, but are not limited to growth factors, receptor tyrosine kinases, non-receptor tyrosine kinases, SER/THR protein kinases, cell surface proteins, cell signaling proteins, guanine nucleotide exchangers and binding proteins, or nuclear proteins, or nuclear transcription factors.

5. Other Agents

It is contemplated that other agents may be used in combination with the present invention to improve the therapeutic efficacy of treatment. One form of therapy for use in conjunction with chemotherapy includes hyperthermia, which is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

Hormonal therapy may also be used in conjunction with the present invention. The use of hormones may be employed in the treatment of certain cancers such as breast, prostate, ovarian, or cervical cancer to lower the level or block the effects of certain hormones such as testosterone or estrogen and this often reduces the risk of metastases.

Adjuvant therapy may also be used in conjunction with the present invention. The use of adjuvants or immunomodulatory agents include, but are not limited to tumor necrosis factor; interferon alpha, beta, and gamma; IL-2 and other cytokines; F42K and other cytokine analogs; or MIP-1, MIP-1beta, MCP-1, RANTES, and other chemokines.

6. Vaccines

It is contemplated that vaccines that are used to treat cancer may be used in combination with the present invention to improve the therapeutic efficacy of the treatment. Such vaccines include peptide vaccines or dendritic cell vaccines. Peptide vaccines may include any tumor-specific antigen that is recognized by cytolytic T lymphocytes. Yet further, one skilled in the art realizes that dendritic cell vaccination comprises dendritic cells that are pulsed with a peptide or antigen and the pulsed dendritic cells are administered to the patient.

Examples of tumor-specific antigens that are being used as vaccines in melanoma include, but are not limited to gp100 or MAGE-3. These antigens are being administered as peptide vaccines and/or as dendritic cell vaccines.

I. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Structure of G-quartet Oligonucleotides

The G-quartet oligonucleotides as used in this delivery study were T30923, T40214 and T40216, SEQ. ID. NO. 1, SEQ. ID. NO. 2 and SEQ. ID. NO. 3, respectively.

FIG. 1 A shows that T30923 forms an intramolecular G-quartet structure with two G-quartets in the middle and two G-T-G-T loops on the top and bottom determined by NMR (Jing et al., 1998). Further evidence to support intramolecular G-quartet formation for T30923 was obtained from non-denaturing gel electrophoresis and from melting and annealing measurements (Jing et al., 2000b).

T40214 was a newly designed oligonucleotide and was expected to form an intramolecular G-quartet structure with two G-quartets in the middle and two G-C-G-C loops on the top and bottom.

Yet further, the G-rich oligonucleotide, T40216, with the sequence of SEQ. ID. NO. 3 also forms intramolecular G-quartet structures, shown in FIG. 1A.

EXAMPLE 2

Circular Dichroism

The G-quartet forming oligonucleotides, intramolecular or intermolecular, give rise to large induced ellipticity values in cirular dichroism (CD) and are characterized by nonconservative spectra with maxim at 264 nm and 210 nm, and minimum at 240 nm (Lu et al., 1992; Gray et al., 1992).

Briefly, CD spectra of the G-quartet oligonucleotides were obtained in 15 μM strand concentration in 10 mM KCl and 20 mM $Li_3PO_4$, at pH 7, on a Jasco J-500A spectropolarimeter at room temperature. Data are presented in molar ellipticity (deg $cm^2$ $dmol^{-1}$).

CD spectra demonstrated (FIG. 1C) that T40214 and T40216 form the same molecular structure as that of T30923 and also showed that a longer G-quartet stem for T40216 corresponds to weaker CD ellipticity at 264 and 240 nm. However, the nonspecific oligodeoxynucleotides (ns-ODN) employed as a control was not form G-quartet structure since the CD of ns-ODN did not show CD ellipticity at 264 and 240 nm. The difference between T40214 and T30923 is the substitution of the residues of cytosine for the residues of thymine in T40214 loop domains, which decreased the binding affinity to $K^+$ ions and increased the efficiency of intracellular delivery (Vakser, 1996).

EXAMPLE 3

Kinetic Measurement

Folding kinetics were obtained with the manual addition of metal ions at t=0, followed by absorption measurement at 264 nm, using hp 8452A UV spectrophotometer. Mixing dead time was about 5 seconds. Kinetics were monitored from 5 seconds to 15 minutes. The folding time constants, τ1 and τ2, were estimated by fitting the UV kinetic curves using the function of a sum of two exponentials, i.e., $A(t)=A_o(\exp(-t/\tau 2)-f*\exp(-t/\tau 1))$, where $A_o=C\epsilon 1$, C is total concentration of oligonucleotide, $\epsilon$ is the extinction coefficient of oligonucleotide sequence, 1 is path length and f is the fitting constant.

Previous NMR data demonstrated (Jing et al., 1997b; Jing et al., 1998) that T30923 folds to an intramolecular G-quartet structure in two steps from open state ($Li^+$-form) to closed state ($K^+$-form) by binding three $K^+$ ions. The first step corresponds to a rearrangement of the bases of the two central G-quartets during the binding to a $K^+$ ion and the second step results from the loop base folding parallel to the bases of the underlying G-quartet by binding an additional $K^+$ between a G-quartet and the adjacent loop domain on the top or bottom (FIG. 1C). The kinetics of UV absorption versus time showed that the structure transition of T30923 was also composed of two steps, corresponding to the two-step transition observed by NMR. The first step is hyperchromic and the second one is hypochromic in UV absorption, respectively.

Figure 3:
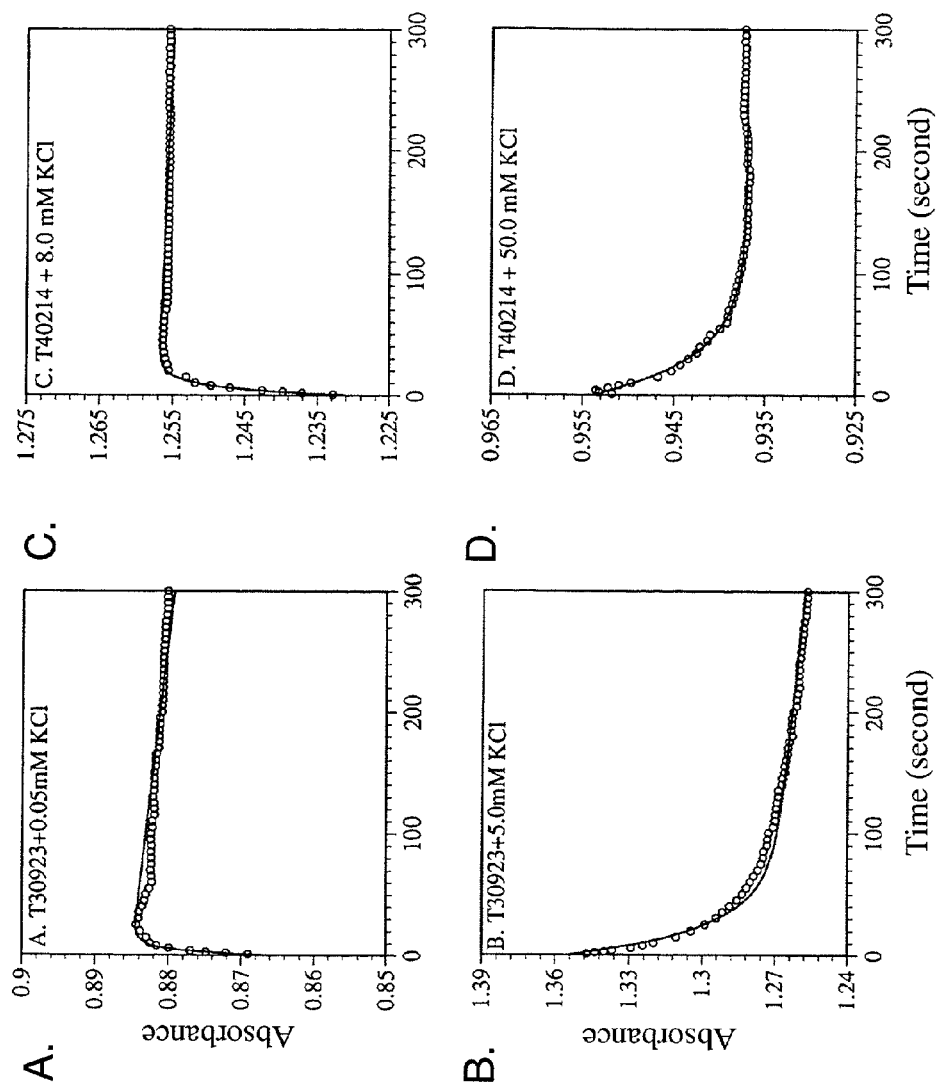
FIG. 3A, FIG. 3B, FIG. 3C and FIG. 3D show kinetics of $K^+$-induced structure transition of G-quartet oligonucleotides. The kinetic curves for T30923 (SEQ. ID. NO. 1) and T40214 (SEQ. ID. NO. 2) were obtained at 0.05 (FIG. 3A), 5.0 (FIG. 3B), 8.0 (FIG. 3C), and 50.0 (FIG. 3D) mM KCl, respectively.

The kinetics of $K^+$-induced structure folding for T30923 and T40214 were shown in FIG. 3. At the $K^+$ concentrations of 0.05 and 8.0 mM (FIGS. 3A & C), the time constants (τ1) of the first step are about 5 and 6 seconds for T30923 and T40214 while the time constants (τ2) of the second step are about $10^4$ to $10^5$ seconds for T30923 and T40214. The large time constants of T2 indicate no second step occurring in these $K^+$ concentrations. When the $K^+$ concentrations were raised to 5.0 and 50.0 mM, respectively (FIGS. 3B & D), the first step became too rapid to be observed with our instruments and the time constants (T2) of the second step decreased to 22 seconds for T30923 and 32 seconds for T40214. The decrease in UV absorption in the second step (FIGS. 3B & D) was caused by an increase in DNA base stacking because the loop bases folded parallel to the bases of the underlying G-quartet to form a compact G-quartet structure.

Although both T30923 and T40214 were shown to form the same G-quartet structure, the significant difference of folding kinetics between the two oligonucleotides was the concentration of potassium inducing the oligonucleotides to form G-quartet structure. The first step for T30923 was observed in 0.05 mM KCl while that of T40214 occurred in 8.0 mM KCl. At 5.0 mM KCl, T30923 formed a compact G-quartet structure with two folded loop domains, however, T40214 formed the same structure at 50 mM KCl. T40214 has a much weaker binding affinity to $K^+$ ions than T30923.

The loop domain of T40214 was expected to form H-bonds as shown in FIG. 1A when an additional $K^+$ coordinated between a G-quartet and the adjacent loop domain. Modeling study predicted that the G-C-G-C loop domain of T40214 can not fold into a plan because of the short distance between C-G bases, which may cause a decrease in the binding affinity to $K^+$ ions.

Thus, the data showed that the difference between the two oligonucleotides is the substitution of the residues of cytosine for the residues of thymine in T40214 loop domains. The substitution was designed to greatly decrease the binding affinity of T40214 to $K^+$ ions. Generally, the $K^+$ ion concentration is 4 mM outside cells and 140 mM inside cell. T30923 folds to a compact G-quartet at 5.0 mM KCl; however, T40214 folds to the same G-quartet structure at 50.0 mM KCl. Thus, T30923 was not well delivered into cells because T30923 molecules refolded to G-quartet structure outside of cells. However, it was expected that T40214 would have a high delivery efficiency because the molecules maintained the unfolded structure before entering cells.

EXAMPLE 4

Gel Electrophoresis

The oligonucleotides, T30923 and T40214, in 10 mM KCl and 20 mM $Li_3PO4$ were heated at 90° C. for 15 minutes and then cooled at 4° C. for one hour for formation of G-quartet structure.

T30923 and T40214 in $H_2O$ were heated at 90° C. for 30 minutes and then gradually cooled down to room temperature for denatured oligonucleotides.

Both the oligonucleotides in G-quartet structure and in unfolded state were labeled with $^{32}P$ using 5'-end labeling procedure and purified using G-25 spin columns. Lipofectin was added to the labeled samples at designed ratio to form lipid-DNA complexes. The lipid-DNA complexes were vortexed and incubated at room temperature for 30 minutes. The 20% non-denaturing polyacrylamide gels were pre-cooled in 4° C. cold room in 1×TBE buffer for an hour. Then the samples with or without lipid were loaded onto the gels and the gels were run in a cold room.

EXAMPLE 5

Lipid-DNA Delivery Test Using Electrophoresis

Non-denaturing electrophoresis was employed for the delivery study, in which the migrational rate of an oligonucleotide depends on the size of its molecular structure.

Briefly, $^{32}P$-labeled oligonucleotides, in denatured state and in G-quartet structure, were incubated with Lipofectin at ratio of lipid/oligo as 5:1 in room temperature for 1 hour. Then, 350 ng of the $^{32}P$-labeled oligonucleotides were added into each cell culture plate containing about $3\times10^5$ cells. The lipid-DNA complexes were incubated with the cells at 37° C. for 24 hours. Next, the cell growth medium, was discarded and the cell plates were washed three times with PBS to remove the oligonucleotides outside of the cells and attached to the cells. Cells were collected in a tube and lysed with lysis buffer. The lysed cells were centrifuged at 15000 rpm for 15 minutes to separate the oligonucleotides from cell debris. Next, ethyl alcohol was added to the supernatant to precipitate the $^{32}P$-labeled oligonucleotides. Pellets were electrophoresed using a 20% non-denaturing polyacrylamide gel.

Figure 4:
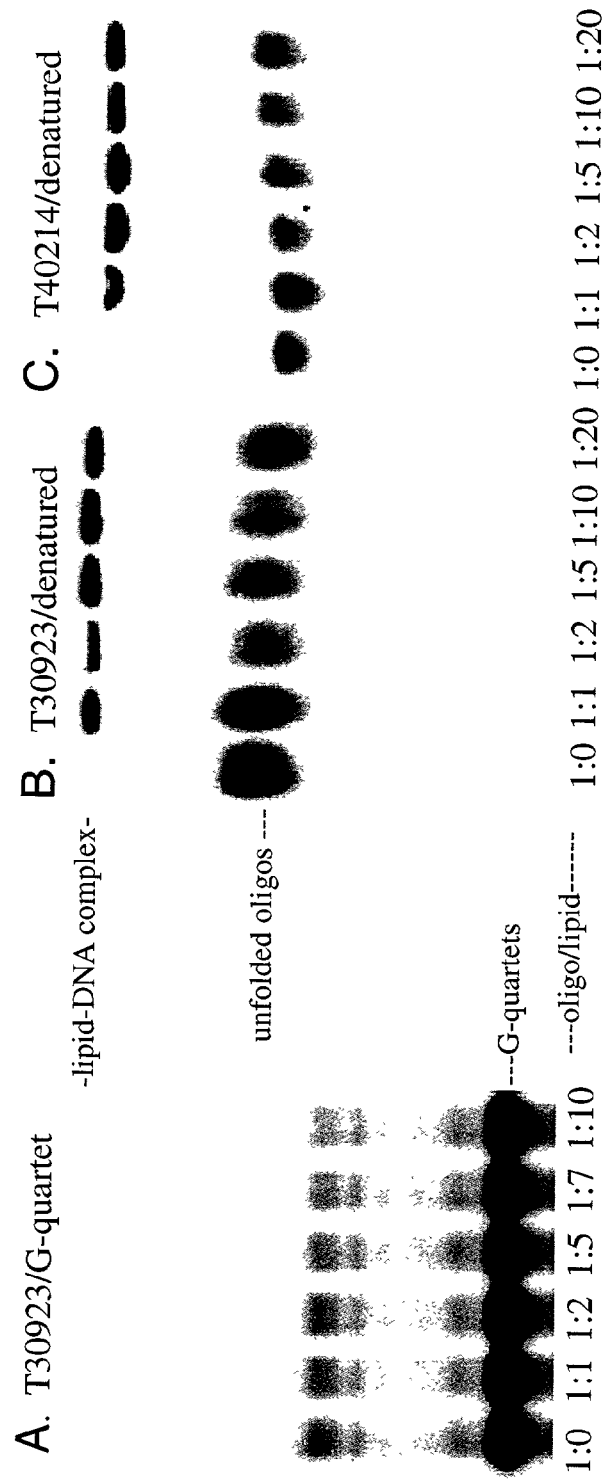
FIG. 4A, FIG. 4B and FIG. 4C show non-denaturing gels of G-quartets-lipid structures.

The different rates of migration of the oligonucleotide in a non-denaturing gel correspond to different molecular structures. The gel of T30923 (FIG. 4A) showed that the intensity of the bottom band, which corresponds to the molecules in G-quartet structure, remained unchanged when T30923 was mixed with Lipofectin at a ratio of oligo/lipid from 1:0 to 1:10. Lipofectin is composed of 1:1 (w/w) liposome formulation of the cationic lipid N-[1-(2,3-dioleyloxy)propyl]-N,N,N-trimenthylammonium chloride (DOTMA) and dioleoyl phosphatidyl ethanolamine (DOPE). The faint bands at the top of the gel corresponded to the molecules of oligonucleotides incorporated with lipid to form lipid-DNA complexes, which have a large size with slow migration (FIG. 4A). A significant difference was observed in FIGS. 4B & C when T30923 and T40214 were totally denatured. Thus, no G-quartet band appeared at the bottom of the gels in FIGS. 4B & C. An intensive band corresponding to lipid-DNA complexes appeared at the top of the gels when the ratio of oligo/lipid was raised from 1:1 to 1:20. Clearly, the denatured molecules of T30923 and T40214 were readily incorporated within lipid micelles to form lipid-DNA complexes.

Figure 5:
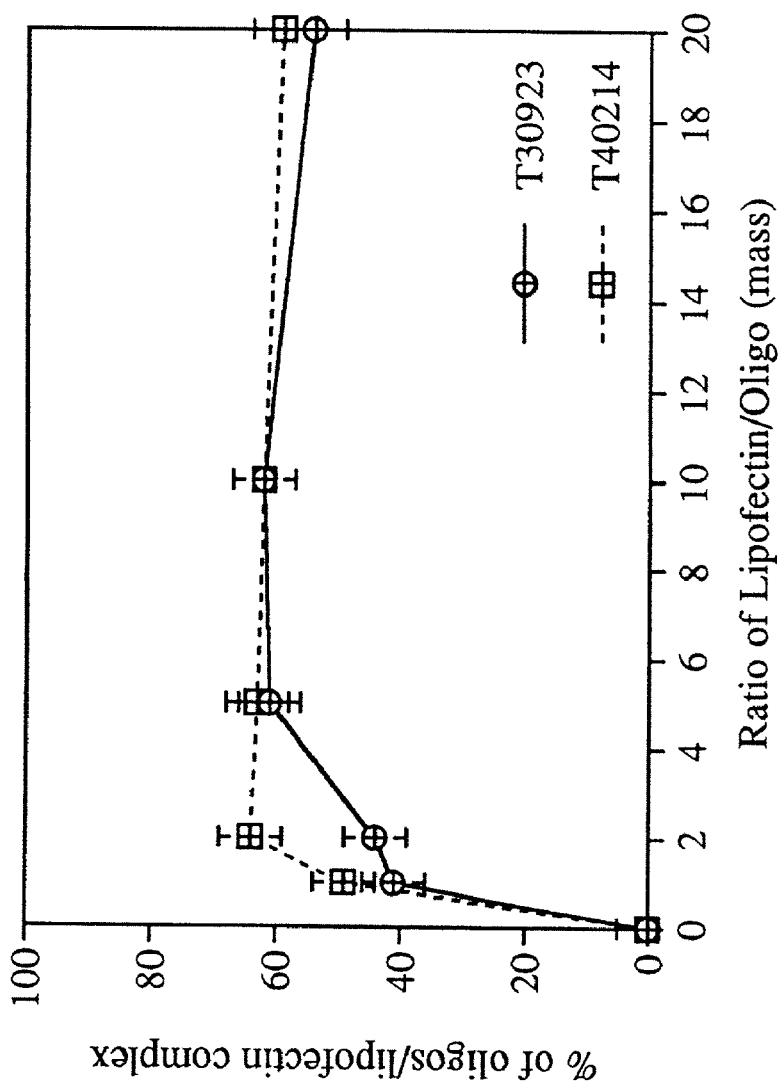
FIG. 5 shows a plot obtained based upon the ratio of the intensities of the top band to that of the top band plus the middle band in FIG. 4B and FIG. 4C versus the ratio of lipofectin/oligo in mass.

Based upon the analysis of the intensities of the two bands, the top and the middle bands in each lane, it was found that more than 60% of the denatured DNA molecules were incorporated into lipid micelles when the lipid/oligo ratio reached 2:1 for T40214 and 5:1 for T30923 (FIG. 5). This data demonstrated that only the G-rich oligonucleotides in the unfolded state can incorporate within liposomes to form a lipid-DNA complex; however, the oligonucleotides in the G-quartet structure do not form lipid-DNA complexes within the liposomes.

Generally, the charge of the complexes was slightly positive to allow interaction with negatively charged cell surfaces, thus increasing the cellular uptake. G-quartets with neutral charge barely incorporate into cationic liposome.

EXAMPLE 6

Intracellular Delivery of G-quartet Oligonucleotides

The same amounts (350 ng) of $^{32}P$-labeled oligonucleotides, T40214 and T30923, in unfolded state and in G-quartet structure were incorporated into Lipofectin at a ratio of lipid/oligo as 5:1. Then, they were incubated in cell plates for 24 hours at 37° C. and each plate contained about $3\times10^5$ cells. Lanes 2 to 5 of the gel were with the labeled oligonucleotides after they were extracted from inside cells.

Figure 6:
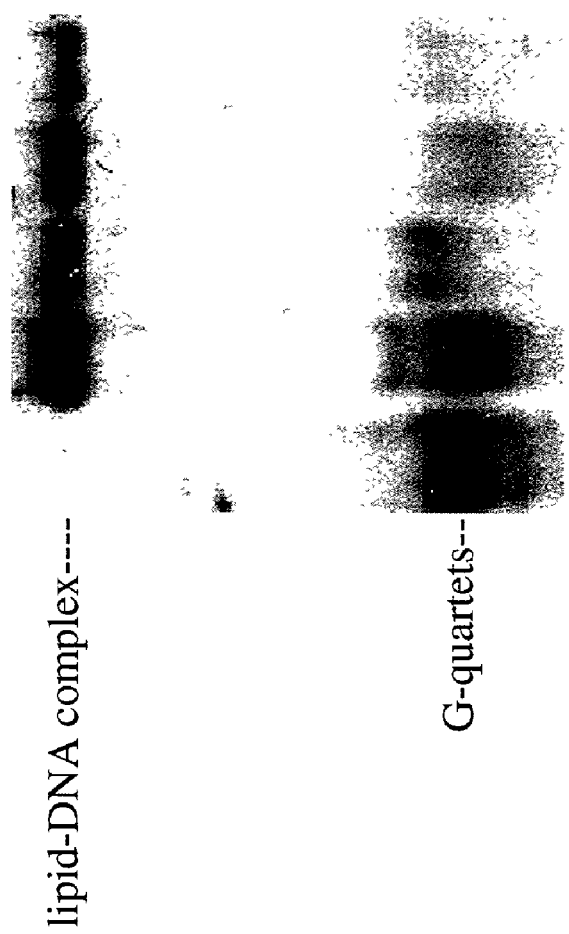
FIG. 6 shows that the molecules of T40214 (SEQ. ID. NO. 2) and T30923 (SEQ. ID. NO. 1) were delivered inside cells by lipid-DNA complexes.

FIG. 6 demonstrated that the molecules of T40214 and T30923 were delivered into cells by lipid-DNA complexes. Lane 1 was T40214 in G-quartet structure without lipid as a control. Lanes 2 and 4 were the molecules of T40214 delivered in unfolded state and in G-quartet structure, respectively. Lanes 3 and 5 used the same strategy for T30923. Compared with the band in Lane 1, the bands at the bottom in Lanes 2 to 5 correspond to the molecules reformed to G-quartet structure inside cells and the bands at top showed the molecules maintaining in lipid-DNA complexes.

Based upon the analysis of the intensities of the two bands from Lanes 2 to 5, it was determined that (Henderson, 1995) the total molecules of T30923 (Lane 3) delivered inside cells was only 47% of that of T40214 (Lane 2). The efficiency of delivering T30923 was much lower than that of T40214. The total molecules of T40214 delivered in G-quartet structure (Lane 4) was about 40% of that delivered in unfolded state (Lane 2) since the molecules in G-quartet structure had a low ratio to form lipid-DNA complexes with lipid. The intensities of the two bands in Lane 2 were about 50% of the total molecules of T40214 inside cells released from DNA-lipid complex to reform G-quartet structures in 24 hours.

Thus, the data demonstrates that intracellular delivery of G-quartet oligonucleotides by DNA-lipid complexes can be divided into three steps: (1) binding and internalization of DNA by the cells, (2) escape of the DNA into the cytoplasm, and (3) entry of the DNA oligos into the nucleus. It is well known and understood that the primary driving force for the binding of the lipid-DNA complex to the cell membrane is electrostatic force. The internalization of the lipid-DNA occurs mainly through endocytosis. DNA oligonucleotides are released into the cytoplasm is most likely caused by the interaction between cationic lipid and anionic molecules presented in the membrane. Yet further, it is contemplated that variation of the charge ratio, incubation time or the component of lipids may increase the percentage and speed of DNA oligonucleotides released from lipid-DNA complexes.

EXAMPLE 7

Microscopy of Biotin-Labeled G-Quartets

T40214 and T30923 were 5' labeled with biotin and were incubated with Lipofectin at ratio of lipid/oligo as 5:1 in room temperature for 1 hour. Next, 350 ng of the labeled oligonucleotides were added to each cell plate. The lipid-DNA complexes were incubated with cells at 37° C. for 24 hours. The cell culture medium was removed and the plates were washed three times with PBS. Next, the cells were lysed by adding 0.5% triton. The lysed cells were fixed to slides using 3.7% formaldehyde. To develop the dye fluorescence of the 5'-biotin-labeled oligonucleotides, the slides were incubated with Avidin-Texas-Red to identify the G-quartet oligonucleotides under microscopy.

The deliveries for T40214 and T30923 in unfolded state were tested in different cell lines, such as 3T3 (FIGS. 7A & B), CEMSS (FIGS. 7C & D) and MT4 (FIGS. 7E & F) cells, respectively. The biotinlabeled oligonucleotide molecules were dyed and the nuclei of cells were counterstained. The color of nuclei changed when oligonucleotide molecules entered into the nuclei. The pictures show that much larger amounts of T40214 molecules than T30923 molecules in unfolded state were transported inside cells and nuclei in different cell lines (FIGS. 7A–F). No oligonucleotide molecules of T40214 and T30923 in G-quartet structure were observed into cells (FIGS. 7G & H), showing that the G-quartet oligonucleotides without lipid deliverers can not penetrate into cells.

Figure 7:
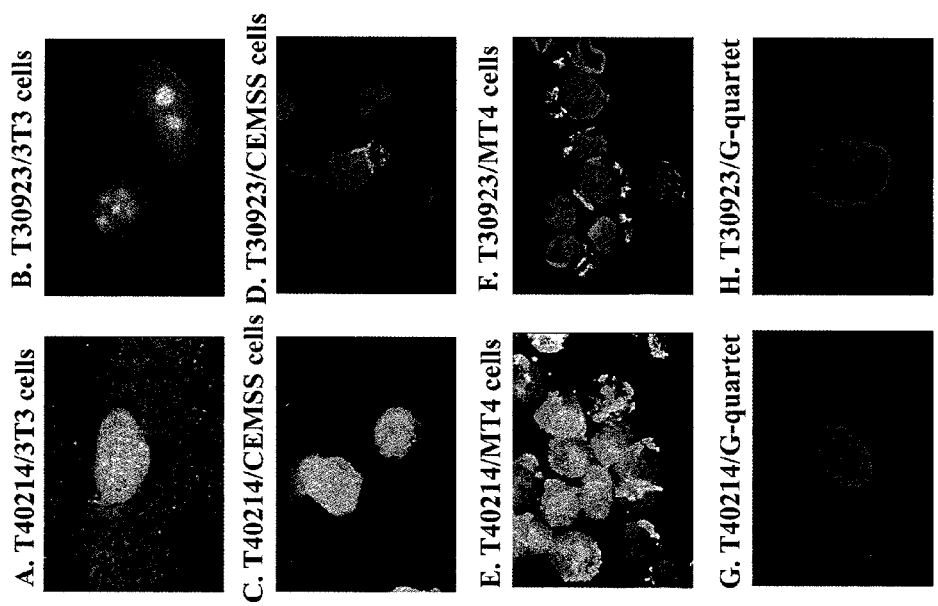
FIG. 7A, FIG. 7B, FIG. 7C, FIG. 7D, FIG. 7E, FIG. 7F, FIG. 7G and FIG. 7H show that the biotin-labeled molecules of T40214 (SEQ. ID. NO. 2) and T30923 (SEQ. ID. NO. 1) delivered into cells and nuclei.

The results observed in FIG. 7 are consistent with that in FIG. 6. The delivery efficiency of G-rich oligonucleotides not only strongly depends on molecular structure, G-quartet or unfolded, but also depends on sequences of G-rich oligonucleotides.

Thus, the data illustrate that molecules of T40214 successfully entered into nuclei after incubating them in cells for 24 hours. The main reason that the refolded G-quartet molecules can penetrate into nucleus is considered to be due to their structural characters. After the oligonucleotide molecules were released from lipid-DNA complexes and entered the cytoplasm, they refolded to form G-quartet structures due to the influence of $K^+$ ions inside the cells. The highly stable and compact G-quartet structure greatly enhances the ability of the oligonucleotides to resist nuclease digestion (Jing 2000b). Thus, the molecules reformed to G-quartet structure have a greater capacity to penetrate into the nucleus through the nuclear pores.

EXAMPLE 8

Effective Intracellular Delivery System

Since the lipid deliverers only can form lipid-DNA complexes with unfolded molecules of the G-rich oligonucleotides (FIG. 4) and also the molecules in G-quartet structure cannot penetrate cell membranes directly to reach their target inside cells (FIGS. 7G & H), a novel deliver system was developed based upon the dependence of potassium-induced formation of G-quartet structure.

Figure 8:
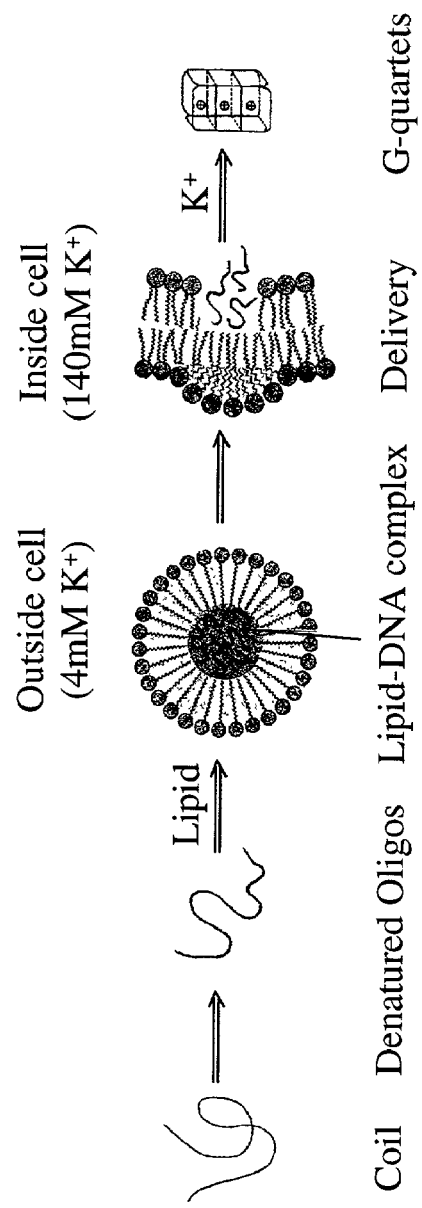
FIG. 8 shows the scheme of intracellular delivery system for G-quartet oligonucleotides.

The difference of $K^+$ concentrations inside (140 mM) and outside (4 mM) cells to induce the G-rich oligonucleotides to form a different structure inside and outside cells was used as the basis for the system. A novel intracellular delivery system for G-quartet oligonucleotides is shown in FIG. 8. This system includes several steps: (i) G-quartet oligonucleotides are denatured in order to increase the probability of incorporation of G-rich oligonucleotides within lipid. (ii) The denatured molecules are mixed with lipid to form lipid-DNA complexes. (iii) The lipid-DNA complexes are incubated with cells and (iv) then the delivered molecules refold to form to G-quartet structure, induced by the action of $K^+$ ions inside cells.

EXAMPLE 9

Enhancement of the Inhibition of HIV-1 Replication by Intracellular Delivery

The inhibitions of HIV-1 IN on strand transfer for T30923 and T40214 were measured in a dual assay, which detected the disintegration of HIV-1 IN. The procedure of integration of the cleaved viral DNA into host DNA by HIV-1 IN is referred to as strand transfer (ST).

In the strand transfer assay, HIV-1 IN was pre-incubated at a final concentration of 400 ng with G-quartet inhibitors for 15 minutes at 30° C. in a reaction buffer containing 25 mM MOPS, pH 7.2, 25 mM NaCl, 7.5 mM $MnCl_2$, 0.1 mg/ml BSA and 14.3 mM β-mercaptoethanol. Then 5 nM of the 5'-end $^{32}P$ labeled duplex oligonucleotides were added to the final volume of 10 μl and incubation was continued for an additional 1 hour. Reactions were quenched by addition of 5 μl of denaturing loading dye. Samples were loaded on a 20% (19:1) denaturing polyacrylamide gel.

Figure 9:
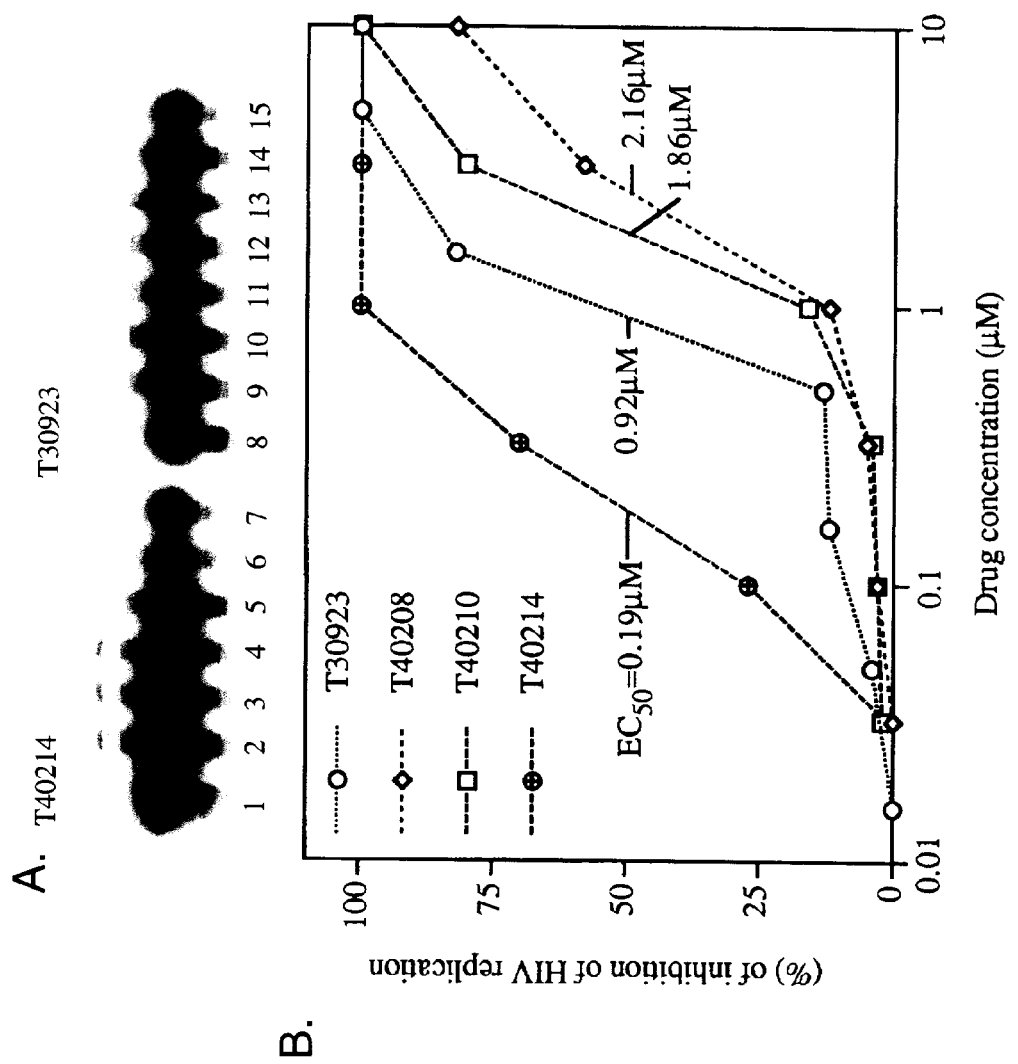
FIG. 9A and FIG. 9B shows that the inhibition of strand transfer (ST) on HIV-1 IN in vitro (FIG. 9A) and the inhibition of HIV-1 (RF) replication in CEMSS infected cells (FIG. 9B).

In Lanes 1 and 8 of FIG. 9A, the strong bands correspond to the duplex oligonucleotide without HIV-1 IN as controls. ST products, which were from joining the 3'-end of one duplex to another, yielded larger molecular species with slower migration. The intensities of the ST bands significantly decreased when the concentration of G-quartets increased from 0 to 500 nM. $IC_{50}$s of the inhibition of ST of HIV-1 IN for T30923 and T40214 are 80 and 40 nM, respectively (FIG. 9A).

The second assay was an assay to evaluate the anti-HIV efficacy in cell lines. Uninfected CEMSS cells were passaged in T-150 flasks for use in the assay. On the day preceding the assay, the cells were split 1:2 and washed twice in tissue culture medium and resuspended in fresh medium. The cells were pelleted and resuspended in tissue culture medium and added to the drug-containing plates in volumes of 50 μl. A pre-titered aliquot of HIV-1 (RF strain) was then resuspended and diluted into tissue culture medium. The amount of virus (or virus plus inhibitors) was added to each well in a volume of 50 μL to measure cell killing at post-infection for 6 days. After 6 days of incubation at 37° C. in a 5% $CO_2$ incubator, the test plates were analyzed by macroscopic observation, using staining with the tetrazolium dye XTT. The results of the macroscopic observation were confirmed by further microscopic analysis to evaluate the activity of the test compounds. Adhesive plate sealers were used instead of the lids, the sealed plate was inverted several times to mix the soluble formazan product and the plate was read by a spectrophotometer at 450 nm. The results of $EC_{50}$ were calculated and plotted as % inhibition of HIV replication verse drug concentration.

FIG. 9B shows plots of inhibition of HIV-1 (RF) replication versus drug concentration for T40214, T30923, T40208 and T40210 in CEMSS infected cells. The G-rich oligonucleotides of T40208 SEQ. ID. NO. 4 (GGGCGGGTGGGTGGGT) and T40210 SEQ. ID. NO. 5 (GGGTGGGTGGGCGGGT) were used as nonspecific controls. Each data point was the average of six measured values. $EC_{50}$s of the inhibition of HIV-1 (RF) replication for T40214 and T30923 in infected cells were 0.19 μM and 0.92 μM, respectively. $EC_{50}$ of T40214 was 5 fold lower than that of T30923. The significant difference of the inhibition of HIV replication between the two oligonucleotides was most likely caused by their intracellular delivery. The high efficiency of intracellular delivery for T40214 greatly decreased HIV-1 replication and increased the probability to target HIV-1 IN in infected cells. T40208 and T40210 were composed by the substitution of a single cytosine for a thymine at residue 4 and 12 of T30923, respectively. These substitutions strongly disrupted the T4-G5-T12-G13 loop structure of T30923 (FIG. 1A), so that they cannot form a compact intramolecular G-quartet structure. The factor that the inhibition of HIV-1 (RF) replication for T40208 ($EC_{50}$=2.16 μM) and T40210 ($EC_{50}$=1.86 μM) were much weaker than that of T40214 provides the evidence that reforming G-quartet structure of T40214 inside cells were also very important for the inhibition of HIV replication.

Thus, the data indicate that the G-quartet molecules without lipid mediated-deliverers cannot penetrate cell membranes to target HIV-1 IN inside cells. These results match the previous studies (Cherepanov et al., 1997; Este et al., 1998), in which the G-quartet oligonucleotide, T30177, in the absence of lipid-mediated deliverers was observed to inhibit the enveloped protein gp120 on the surface of cells instead of HIV-1 IN inside cells. Failure to target HIV-1 IN within cells was probably due to its inability to penetrate cell membrane.

The intracellular delivery system of the present invention includes two critical steps: (i) denaturing G-quartet structure in order to form a lipid-DNA complex with lipid, so that the molecules are delivered into cells; and (ii) inducing the delivered molecules to reform G-quartet structure by potassium inside cells. Since the G-quartet structure is the primary requirement for inhibition of HIV-1 IN activity, the present invention is able to deliver the G-quartet into the nucleus so that it can inhibit HIV-1.

Thus, the present invention greatly increased the probability of the intracellular inhibition of HIV-1 IN for G-quartet oligonucleotides and also provided a critical information for drug design that was to design potent G-quartet HIV inhibitors with structure folding in potassium concentration between 4 to 140 mM.

EXAMPLE 10

Intracellular Delivery in Primary Cells

Monkey Primary Cells were grown in stock cultures under standard conditions: 37° C., 5% $CO_2$ in DMEM with 10% FBS in nontissue culture plates. Before culture, the plates were coated with 1 μg of anti-CD3 antibody and 1 μg of anti-CD28 antibody in 1 mL of PBS at 37° C. for 2–3 hours. Two sub-confluent 60 mM dishes without contamination were obtained by overnight culture. The free cells were then placed in sterile 15 mL conicals and centrifuged at 2000 rpm at RT for 5 min. The supernatant was decanted and the pellet was re-suspended in the approximately 250 μL which remained the samples into a single 15 mL conical, and the total volume of cell culture was brought up to approximately 2 mL. In order to have 30000 cells per dish in a six-well or 35-mm tissue culture plate, the highly density cell stock was counted in the mixture of 50 μL of the stock and 50 μL of trypan blue after the cells were incubated for 5 min at room temperature.

Next microscopy was performed by adding 350 ng of 5'-biotin-labeled oligonucleotides, T40214 and T30923, mixed with Lipofectin (LIF) or polyethyleneimine (PEI) at ratio of lipid/oligo as 3:1 into the cell plates. The lipid-DNA complexes were incubated with cells at 37° C. for 24 hours. The cell culture medium was removed. The cells were cytospined on a microscope slide and the slides were washed three times with PBS. The cells were lysed for 2 minutes by adding 0.5% triton and fixed on slides for 15 minutes in 3.7% formaldehyde. To develop the dye fluorescence in the 5'-biotin-labeled oligonucleotides, the slides were incubated at room temperature for 1 hour using Texas-Red dye-conjugated Streptavidin for biotin-labeled oligonuceotides and then incubated at room temperature for 5 minutes using DAP-I for cells nuclear. The cells were washed to eliminate free fluorescence and the G-quartet oligonucleotides were identified under microscopy.

Figure 10:
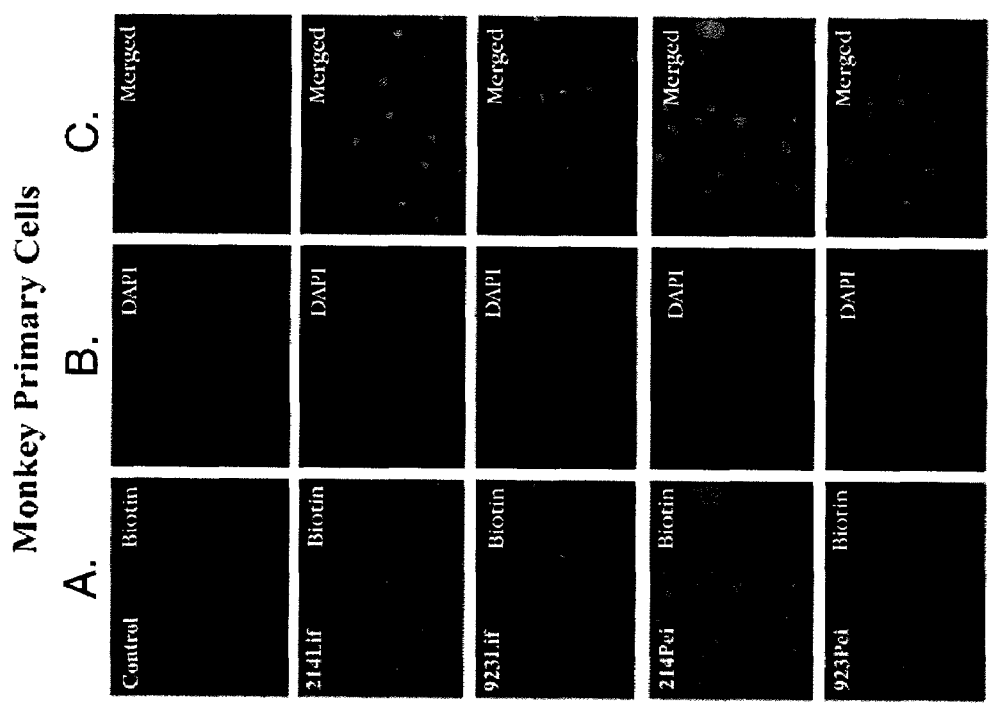
FIG. 10A, FIG. 10B and FIG. 10C show that 5'-biotin-labeled T40214 (SEQ. ID. NO. 2) and T30923 (SEQ. ID. NO. 1) were delivered to the nuclei of monkey primary cells.

FIG. 10 demonstrates that the G-quartet HIV inhibitors, T40214 and T30923, were successfully delivered into monkey primary cells. FIG. 10A shows the molecules of biotin-labeled G-quartet oligonucleotides, T40214 and T30923, which were dyed in Texas-Red, delivered into monkey primary cells by lipid deliverers, Lipofectin (LIF) and polyethyleneimine (PEI). FIG. 10B shows that the nuclei of the monkey primary cells were dyed using DAP-I. FIG. 10C demonstrates the results of FIG. 10A and FIG. 10B merged together. The color of nuclei changed when the oligonucleotide molecules entered inside the nuclei. The pictures show clearly the G-quartet HIV inhibitors were well delivered into monkey primary cells and nuclei, especially for T40214.

Figure 13:
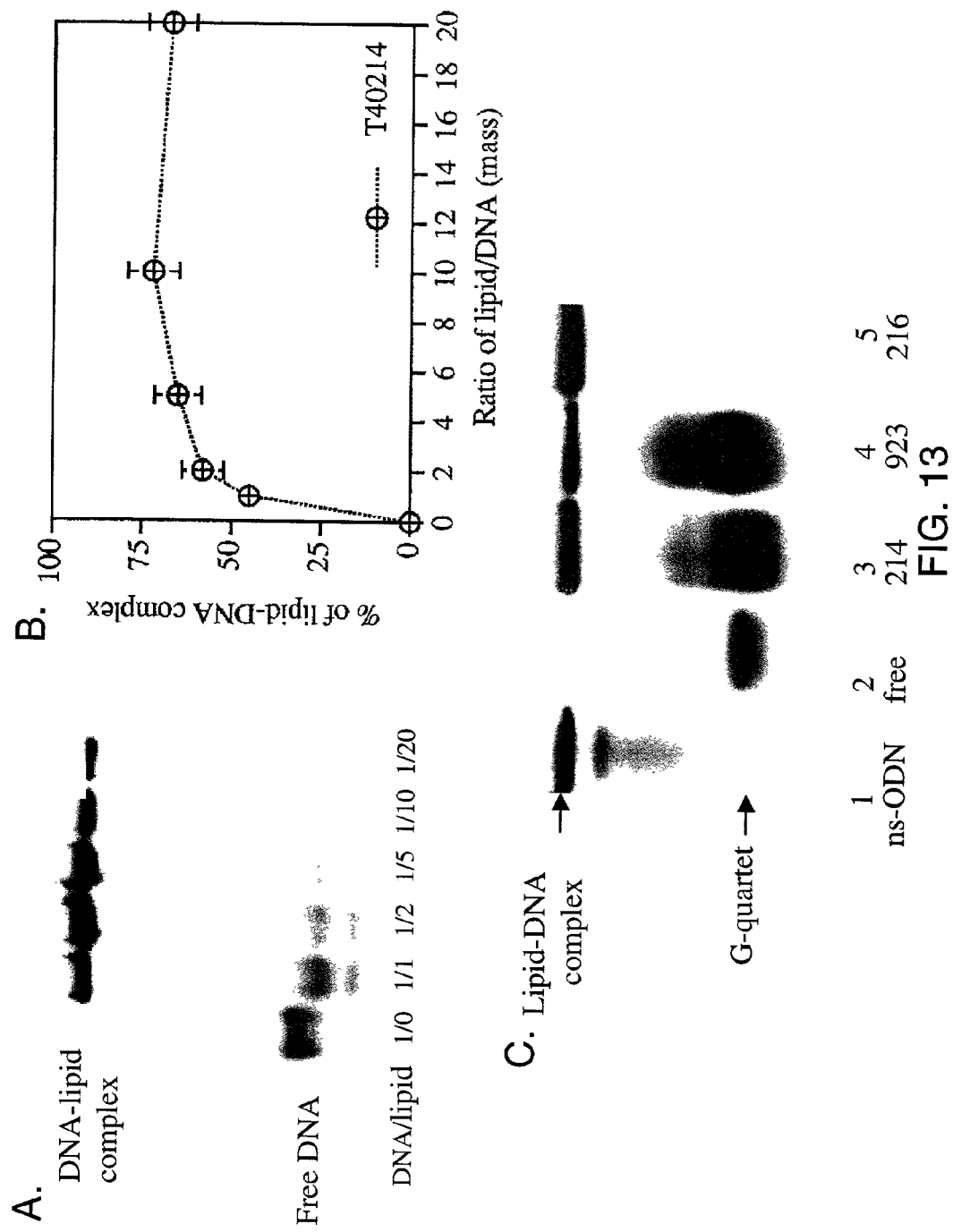
FIG. 13A, FIG. 13B and FIG. 13C show the delivery of lipid-DNA.

Compared with the two G-quartet inhibitors, T40214 and T30923, delivered by the same lipid, the pictures in the left column show that the efficiency of intracellular delivery for T40214 was much higher than that for T30923, consistent with the observation in other cell lines. Also FIG. 13 shows that PEI as lipid deliverer seems to have a better intracellular delivery than LIF. Thus, the present invention demonstrates that a G-quartet, such as T40214 was well delivered in the nuclei of monkey primary cells, which strongly supports that T40214 is a promising candidate of HIV-1 IN inhibitor for further pre-clinical and clinical tests.

EXAMPLE 11

Assay of Inhibition of STAT3 and STAT1 In Vitro

Based upon the mechanism that the cytokine receptors, such as IL-6 or INFs, induce JAK-mediated tyrosine phosphorylation of STATs to form the phosphorylated dimers and then the dimers translocate to the nucleus and bind to DNA elements, an assay of inhibition of DNA binding activity of STAT3 and STAT1 was designed and performed Briefly, IL-6 (25 ng/mL) or INFγ(10 ng/mL) was added into the wells containing 5~7×$10^5$ HepG2 cells and incubated at 37° C. for 20 minutes. The cytosolic extraction was performed, including washing each well two times with PBS. The cells in each well were scraped off and the cell pellet was obtained by centrifugation (6000 rpm for 1 min).

Cells were resuspended in 50 μL high salt buffer (20 mM Hepes (pH7.5), 10 mM KCl, 0.1 mM EGTA, 0.1 mM EDTA, 1 mM DTT, 0.5 mM PMSF, 1 μg/mL leupeptin, 1 μg/mL Aprotinin, 420 mM NaCl, 8 20% Glycerol). To lyse the cells, the cells were frozen and thawed for 4–5 times on dry ice and ice. Centrifugation was carried out at 12000 rpm for 20 minutes at 4° C. and the supernatant was obtained and stored at −80° C. for further usage. The $p^{32}$ labeled DNA probe (hSIE, SEQ. ID. NO. 6: 5'-AGCTTCATTTCCCG-TAAATCCTA) was purified using G-25 columns (Amersham Pharmacia Biotech Inc). The $p^{32}$ labeled DNA probe was mixed with 5 μg of cell supernatant, 1× binding buffer and 2 μg of polydidc and incubated in room temperature for 15 minutes. Then 10 μL of G-quartet oligo inhibitors at different concentrations were added to the samples and incubated an additional 30 minutes in room temperature. The reacted samples were loaded into 5% polyacrlamide gel containing 0.25×TBE and 2.5% glycerol. The gel was run under 160–200 V for 2–3 hours at room temperature.

Figure 11:
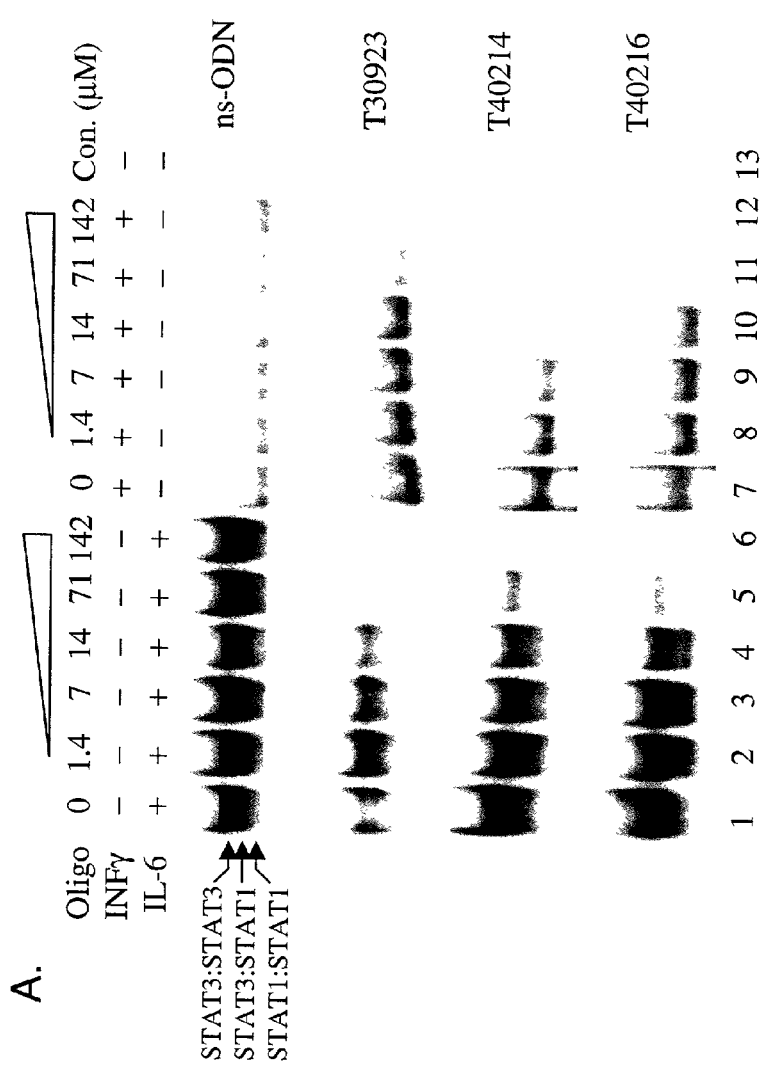
FIG. 11A and FIG. 11B show the inhibition of DNA-binding activity of STAT3 and STAT1 induced by IL-6 and INFγ, respectively.
Figure 11:
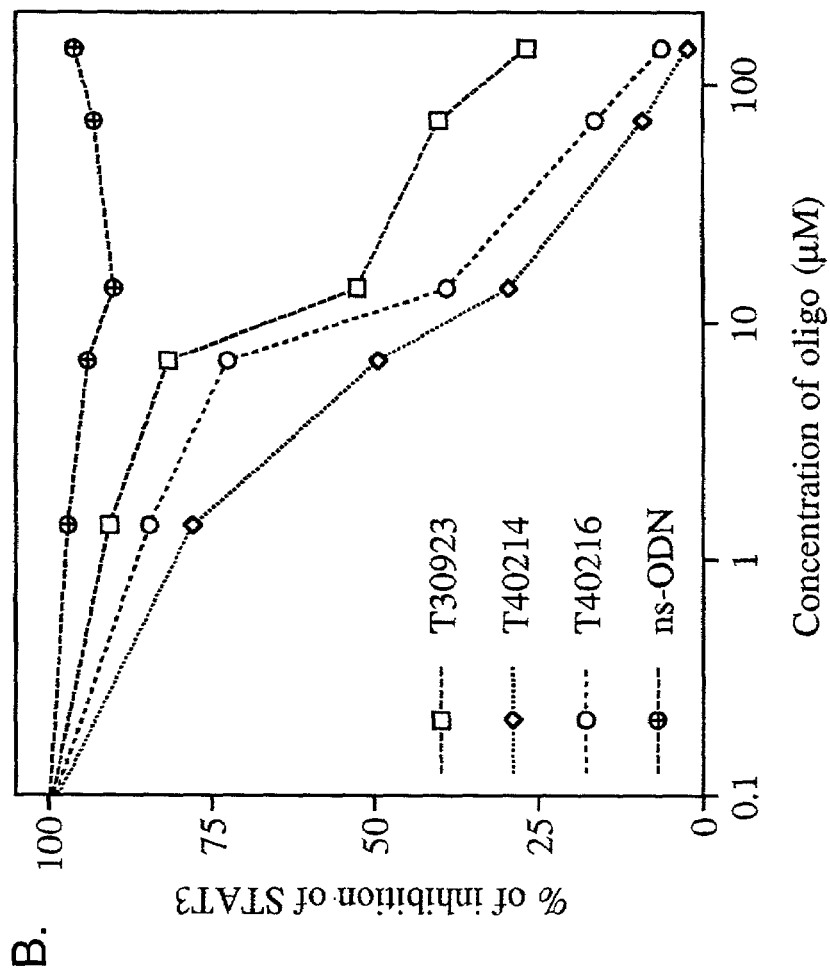
Figure 11:
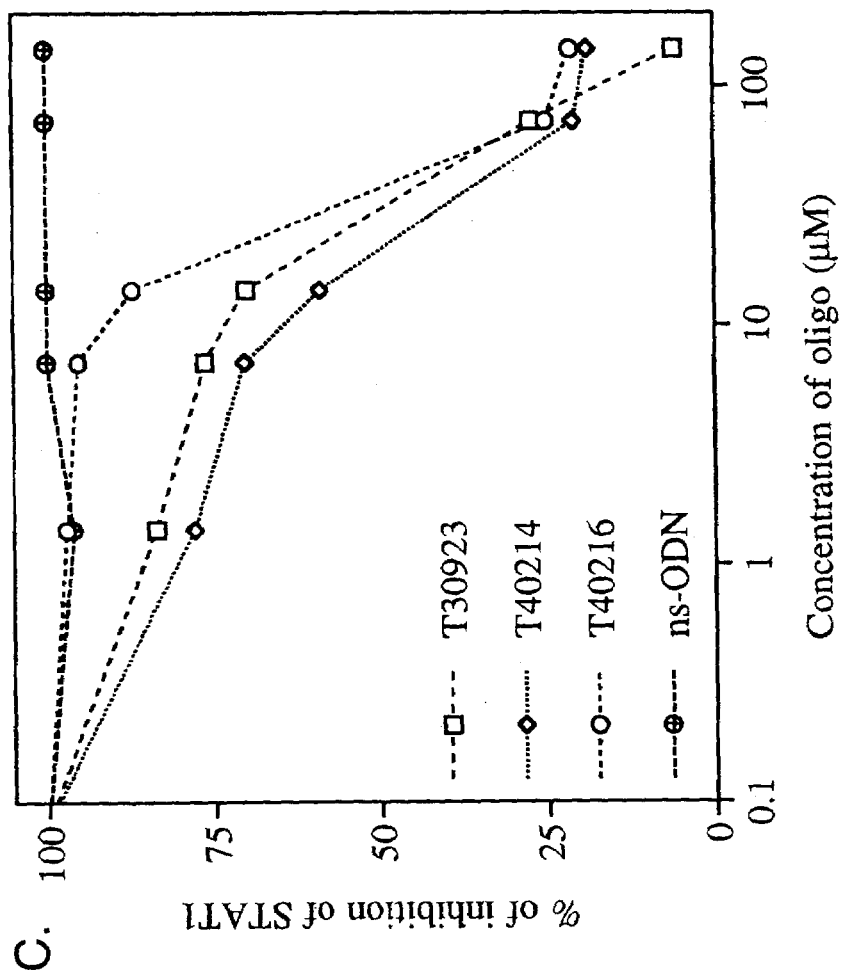

IL-6 was added in HepG2 cells for testing the DNA-binding activity of STAT3. Although IL-6 induced activation of the three STAT dimers, such as STAT3:STAT3, STAT3:STAT1 and STAT1:STAT1, the concentration of DNA bound in STAT3 dimers is much higher than in STAT1 dimers (FIG. 11A). Thus, the IL-6 induced bands were used to detect the DNA-binding activity of STAT3.

INFγ was added in HepG2 cells for testing the DNA-binding activity of STAT1 because INFγ only induced activation of STAT1:STAT1 dimer. After the cells were lysed, the labeled DNA probe (hSIE) was added to react with the cell supernatant for 15 minutes, so that the DNA duplexes can firstly occupy the DNA-binding sites of STAT dimers. Then the G-quartet oligonucleotides as inhibitors were added into the DNA-bound samples to block DNA-binding activity of STATs, called as post-inhibiting procedure. FIG. 11A shows the inhibitions of DNA-binding activity of STAT3 and STAT1 for the oligonucleotides. Lanes 1–6 and 7–12 display the DNA-binding bands of STAT3 and STAT1 dimers induced by IL-6 and INFγ, respectively. Lane 13 is a control without adding IL-6 and INFγ. The concentrations of the oligonucleotides, ns-ODN, T30923, T40214 11 and T40216, as inhibitors were increased from 0 to 142 μM. The bands corresponding to DNA-binding activity were scanned and quantified by densitometric analysis.

The plots of inhibition of STAT3 (FIG. 11B) and STAT1 (FIG. 11C) binding DNA versus concentration of oligo show that ns-ODN has no ability to inhibit the DNA-binding of STAT3 or STAT1 dimers. The 50% inhibitory concentration ($IC_{50}$) of STAT3 for T30923, T40214 and T40216 were 25, 7 and 12 μM and the $IC_{50}$ of STAT1 for T40214 and T40216 are 41, 27 and 48 μM, respectively (Table 1).

TABLE 1

| Compound | $IC_{50}$ to STAT3 | $IC_{50}$ to STAT1 |
| --- | --- | --- |
| T30923 | 25 | 41 |
| T40214 | 7 | 27 |
| T40216 | 12 | 48 |
| Control | — | — |

The data confirmed the three G-quartet oligonucleotides, T30923, T40214 and T40216, having strong inhibitions of the DNA-binding activities of STAT3 and STAT1 and also demonstrated that only the oligonucleotides forming G-quartets have abilities to inhibit the activation of DNA-binding of STAT3 and STAT1. Therefore, an intramolecular G-quartet structure appeared to be a primary requirement to inhibit the DNA-binding activity of STAT dimers.

Comparing $IC_{50}$s with one another, T40214 was the most active inhibitor in the three G-quartets. The fact that the inhibition of DNA-binding activity of STAT1 for T40214 ($IC_{50}$=27 μM) was about four times higher than that of STAT3 ($IC_{50}$=7 μM) provided an evidence that T40214 has a kind of preference to interact with STAT3 dimers rather than STAT1 dimers. The inhibition of DNA binding activity of STATs for the G-quartets was observed in the post-inhibiting procedure, which allowed DNA duplexes to occupy the DNA-binding site firstly. Therefore, the most possible interaction between STAT dimers and G-quartets was considered to occur in the SH2 domain of STATs and to break the dimer formation.

EXAMPLE 12

Mechanism of the Inhibition of DNA-Binding of STATs for G-Quartets

To explore the structure-activity relationship for a drug design, a structure model of activated STAT3 dimer based upon the crystal structure of STAT3 was developed (Becker et al., 1998).

Briefly, the original molecular structure of STAT3 was obtained from Protein data Bank (Becker et al., 1998). The coordinated files of the structures of two STAT3 monomers were modified into a new file for a structure of STAT3 dimer without disrupting original structures, so that the designed drugs can be docked into the structure of activated STAT3 dimer to screen and estimate drug activity. The docking calculations were carried out in SGI computer work-station using INSIGHT II program.

Figure 12:
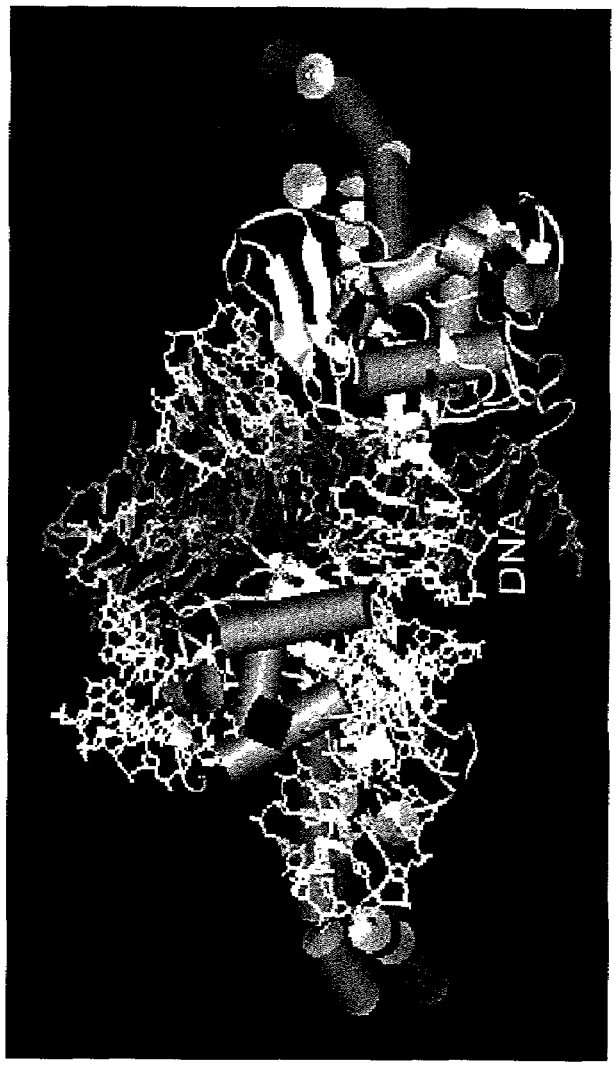
FIG. 12A and FIG. 12B shows the complex structures of G-quartets, T30923, and STAT3 dimer obtained from the statistical docking calculation.
Figure 12:
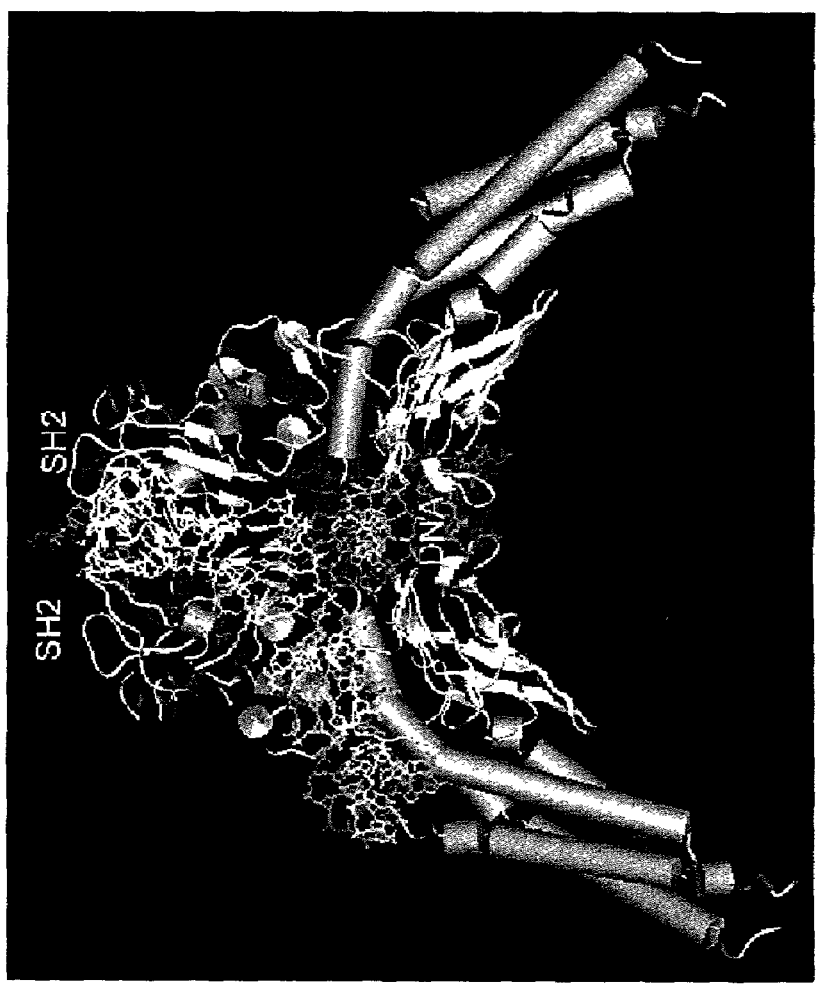

The NMR structure of T30923 (original named as T30695) (Jing and Hogan, 1998) was docked into the model of activated STAT3 dimer including a 20 base-pair DNA duplex, using GRAMM docking program with a high resolutional matching mode (Katchalski-Katzri et al., 1992; Vakser, 1992). The docking range of the calculation was set up from amino residue 300 to 716 of one monomer continuing to amino residue 716 to 300 of the other of the STAT3 dimer. The structure-activity relationship was determined by analysis of the H-bond formation between the model of STAT3 dimer and G-quartet inhibitor in each docking structure. 2000 possible structures of a STAT3 dimer and T30923 complex were obtained from the random docking calculations and total 79145H-bonds were calculated in the 2000 complex structures. Based upon a statistical calculation, it was determined that 40% of total H-bounds (31252H-bonds) were formed between the G-quartet inhibitor and SH2 domain of STAT3 dimer from residue 560 to 680 and 25% of total H-bonds (20399H-bounds) were developed between the inhibitor and DNA duplex bound in DNA-binding site of STAT3 dimer (FIG. 12). Yet further, it was determined that 10 G-quartets interacted with the STAT3 dimer. Several G-quartets were observed to insert between the two SH2 domains of STAT3 dimer. Clearly, the SH2 domains of STAT3 dimer are the main domains that the G-quartet oligonucleotides could interact with.

The statistical docking data explored the mechanism of inhibition of DNA binding activity of STAT3, which could occur in two ways: (1) G-quartet inhibitors interact the SH2 domain to break the dimer formation and (2) G-quartet oligonucleotides compete with DNA duplexes to occupy the binding site. Based upon the crystal structure, the DNA-binding site adopted a 20 base-pair DNA duplex with the length of 70 Å and a diameter of 20 Å (Becker et al., 1998). The post-inhibiting procedure could make the G-quartets hardly compete with a large DNA duplex to occupy the binding site. The crystal structure observed that the residues 591, 609, 611 and 613 formed direct polar interaction with phosphotyrosine 705 and the region from residue 643 to 648 points to other monomer (Becker et al., 1998). These residues were strongly conserved in all SH2 domains. When the interaction occurred between G-quartets and the SH2 domain, the G-quartet inhibitors could block the phosphotyrosine binding and loose the dimer association, matching the observation from the assay of inhibition of STAT3 and STAT1.

EXAMPLE 13

Liposome Formation Using PEI

Briefly, the DNA oligonucleotides, such as T40214, in $H_2O$ were heated at 90° C. for 15 minutes and then gradually cooled down to room temperature for denaturation. The DNA oligonucleotides were labeled with $^{32}P$ using 5'-end labeling procedure and purified using G-25 spin columns. Liposome, polyethyleneimine (PEI), was added in the labeled samples at designed ratio to form lipid-DNA complexes. Then, lipid-DNA complexes were vortexed and incubated at room temperature for 30 minutes. A 20% non-denaturing polyacrylamide gel was pre-cooled in 4° C. cold room in 1× TBE buffer for an hour. Then, the samples with or without lipid were loaded into the gels and the gels were run in cold room.

The non-denaturing gel of T40214 (FIG. 13A) showed that the bands corresponding to the free DNA molecules appeared at the bottom. When lipid was added from the ratio of oligo/lipid as 1:1 to 1:20, an intensive band appeared at the top of each lane corresponding to the formation of lipid-DNA complexes since the complexes have a large size with slow migration. Based upon the analysis of all the intensities of the bands in each lane, it was found that more than 60% of the denatured DNA molecules were incorporated into lipid when the oligo/lipid ratio reached 1:2 for T40214 (FIG. 13B). Selecting a lower ratio of oligo/lipid with a higher efficiency of delivery was critical for decreasing drug toxicity caused by lipid. Hence, the ratio of oligo/lipid at 1:2 was used for intracellular delivery of G-quartet oligonucleotides.

EXAMPLE 14

Intracellular Delivery of G-quartet Oligonucleotides Using PEI

Briefly, 700 ng of $^{32}P$-labeled oligonucleotide was incorporated into PEI at a ratio of 1:2 and then they were incubated in the wells containing $5×10^5$ cells for 24 hours at 37° C. After they were extracted from cells. The labeled oligonucleotides, ns-ODN, T40214, T30923 and T40216, were loaded into Lanes 1, 3, 4 and 5 of the non-denatured gel, respectively. Lane 2 is T40214 in G-quartet structure without lipid as a control.

FIG. 13C demonstrated that the molecules of T40214, T30923, T40216 and ns-ODN were delivered into HepG2 cells by lipid-DNA complexes. Based upon the densitometric analysis of the bands of Lanes 1, 3, 4 and 5, it was determined that about 30% of T40214 (33%) and T30923 (31%), 20% of ns-ODN and 14% of T40216 were released from lipid-DNA complexes into cytoplasm of HepG2 cells in 24 hours. T40216 with a longer G-quartet stem appears to have a difficulty being released from lipid-DNA complexes. Comparing with the free G-quartet molecules in Lane 2, the most released molecules of T40214 and T30923 reformed into G-quartet structure. However, the released molecules of ns-ODN in Lane 1 did not form any specific structures. The results provided the solid evidence to support the intracellular delivery system for G-quartet forming oligonucleotides.

EXAMPLE 15

Inhibition of DNA-Binding Activity of STAT3

The inhibition of DNA-binding activity of STAT3 for the G-quartet oligonucleotides in HepG2 was demonstrated by electrophoretic mobility shift assay (EMSA).

Briefly, Each well of 6-well plates containing about $5~7×10^5$ cells was washed twice with fresh medium. The lipid-DNA complexes, composed of G-quartet oligonucleotides with PEI at the ratio of oligo/lipid as 1:2, were added into each well at designed concentration. After cultured 3 hours, the cell wells were washed twice with fresh medium again to eliminate the lipid-DNA complex outside of cells. Then, 2 mL of 10% fresh medium was added to each well and the cells were cultured. IL-6 (25 ng/mL) or INFγ(10 ng/mL) was added into each well and incubated at 37° C. for 20 minutes before harvesting the cells. Then the cytosolic extraction was carried out and the procedure was the same with the assay in vitro. 2 μL of supernatant obtained from each well was added into 200 μL of protein-assay reagent to measure the total protein concentration in a microplate reader (Model 550). The $p^{32}$ labeled DNA probe (hSIE) was purified using G-25 columns and mixed with 51 g of cell supernatant, 1× binding buffer and 2 μg of polydidc and then incubated in room temperature for 20 minutes. The samples with equal amount of total protein (41 g) were loaded into a 5% polyacrlamide gel containing 0.25×TBE and 2.5% glycerol and the gel was run under 160–200 V for 2–3 hours at room temperature.

Figure 14:
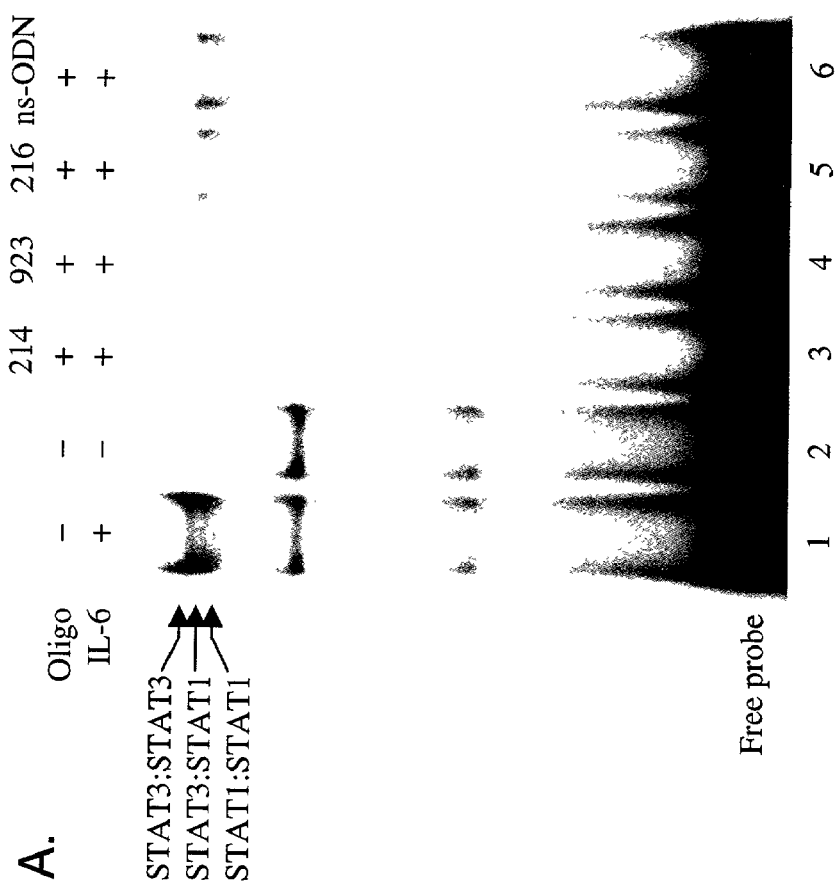
FIG. 14A, FIG. 14B and FIG. 14C show the inhibition of DNA-binding activity of STAT3 in human heptoma (HepG2) cells for T30923 (SEQ. ID. NO. 1), T40214 (SEQ.
Figure 14:
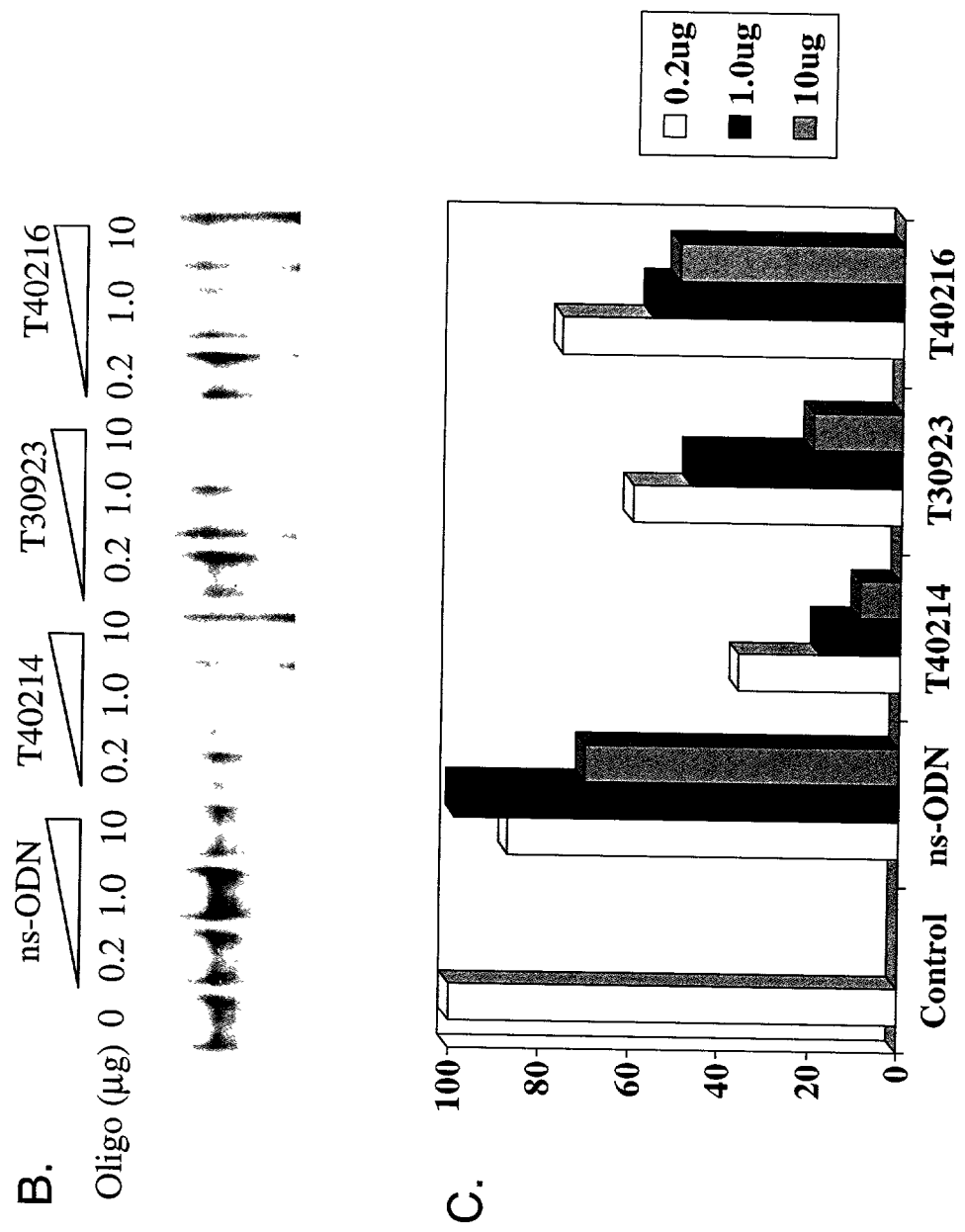

As seen in FIG. 14, Lanes 1 and 2 were the positive and negative controls, with and without adding IL-6. Lanes 3–6 showed the inhibition of DNA-binding activity of STAT3 by 10 mg of T40214, T30923, T40216 and ns-ODN, respectively. Analysis indicated that the intensities of the bands corresponding to STAT3 dimer in Lane 3 and 4 were about 10–20% of that in Lane 1 and the intensities of the bands in Lane 5 and 6 were about 50% and 70% of that in Lane 1, respectively. The concentration-dependent inhibition of DNA-binding activity of STAT3 for the four oligonucleotides were demonstrated in FIG. 14B and FIG. 14C. T40214 inhibited about 64%, 82% and 91% of the DNA-binding activity of STAT3 in about $5×10^5$ HepG2 cells when its concentration was increased from 0.2 to 10 mg. However, T40216 only inhibited about 24%, 45% and 50% of the activation of STAT3 in the concentrations of 0.2, 1.0 and 10 mg, respectively. The week inhibition of activation of STAT3 for T40216 was caused by a lower efficiency of intracellular delivery.

EXAMPLE 16

In vivo Administration of G-Quartets

Generally, the in vivo tests are preformed using the following procedure. First, the G-quartets are labeled 5' with fluoresein, such as T40214, T30923 and ns-ODN SEQ. ID. NO. 7: 5'-TGCCGGATCAAGAGCTACCA). Next, the oligonucleotides are dissovled in H$_2$O and heated at 90° C. for 15 minutes. After the oligonucleotides are cooled to room temperature, the oligonucleotides are mixed with PEI at ratio of oligo/lipid as 1:2. Next, the prepared oligonucleotides are injected into the mice. After about 24 hours, the mice are sacrificed and tissues are removed and frozen. Tissues that may be removed include for example, blood, lung, heart, ovaries, prostate, brain, liver, kidneys, etc. Finally, the tissues are viewed using microscopy to detect the fluorescence, thereby determining the drug distribution in mouse body.

EXAMPLE 17

In Vivo Administration of G-quartets as an Anti-Cancer Agent

Once the drug distribution of G-quartets is determined, the next step is to perform in vivo experiments using specific animal models. Animal models may include animal models for cancer e.g., prostate or breast cancer.

The oligonucleotides are given to the animal. The efficiency of inhibition of STAT3 in the animal and the toxicity of the oligonucleotide or lipid is determined. These results are used to screen for the most potent G-quartet oligonucleotide and the most effective lipid as a deliverer.

Yet further, derivatives of T40214 may be developed. The derivatives are based upon the structure-based drug design system similar to Example 12. These derivatives can be used to find the best G-quartet oligonucleotide for cancer therapy.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

REFERENCES

All patents and publications mentioned in the specifications are indicative of the levels of those skilled in the art to which the invention pertains. All patents and publications are herein incorporated by reference to the same extent as if each individual publication was specifically and individually indicated to be incorporated by reference.

Asante-Applah, E. & Skalka, A. M. (1999) *Adv. Virus Res.* 52, 351–369.
Bangham, et al., *J. Mol. Biol.*, 13:238–252, 1965.
Becker S. et al., (1998) *Nature* 394, 145–151.
Bock, L. C., et al., (1992) *Nature* 355, 564–566.
Canfield et al., *Methods Enzymol.* (1990) 189:418–22.
Cellert, M., et al., (1962). *Proc. Natl. Acad. Sci. USA* 48, 2013-
Cherepanov, P. et al., (1997) *Mol. Pharmacol.* 52, 771–780.
Chesnoy, S. & Huang, L. (2000) *Annu. Rev. Biophys. Biomol. Struct.* 29,27–47.
Craigie, R. (2001) *J. Boil. Chem.* 276, 23213–216.
De Clercq, E. (2000) *Rev. Med. Virol.* 10, 255–277.
Deamer and P. Uster, In Liposomes (M. Ostro, ed.), Marcel Dekker, Inc., New York (1983), pp. 27–52.
El-Gorab et al., *Biochim Biophys Acta.* (1973) 306:58–66.
EPO 0273085
Fraley and Fornari Kaplan, Proc. Nat'l. Acad. Sci. USA 76:3348–3352, 1979.
Gabizon et al., *Cancer Res.* (1990) 50:6371–8.
Ghosh and Bachhawat, In: Wu G. Wu C ed., Liver diseases, targeted diagnosis and therapy using specific receptors and ligands, New York: Marel Dekker, pp. 87–104, 1991.
Gilber, D. E. & Feigon, J. (1999) Current Opinion Structura. Biol. 9, 305–314.
Gray, D. M., (1992) et al., *Methods Enzymol.* 211, 389–406.
Gregoriadis G. and Davis C. Biochem Biophys Res Commun., 89(4):1287–1293, 1979.
Gregoriadis, G. DRUG CARRIERS IN BIOLOGY AND MEDICINE, (ed.), 1979, pp. 287–341.
Hara T, et al., *Biochim Biophys Acta.* (1996) 1278:51–8.
Henderson, E. (1995). In Telomeres p 11–34. Cold Spring Harbor Laboratory Press.
Hogan, M. E. (1995). J. Biol. Chem. 270, 1754–1760.
Jing N. (2000) Expert Opinion on Investigational Drugs 9(8), 1777–1785.
Jing, N., and Hogan, M. E. (1998) J. Biol. Chem. 273, 34992–34999.
Jing, N., et al., (1997a) *Biochemistry* 36, 12498–12505.
Jing, N., et al., (1997b) J. Biomol, Struct. & Dyn. 15, 573–585.
Jing, N., et al., (2000b) J. Biol. Chem. 275, 21460–21467.
Kaneda et al., *J Biol. Chem.*, 264(21):12126–12129, 1989.
Kaneda et al., *Science*, 243:375–378, 1989.
Katchalski-Katzri E, et al., (1992) *Proc. Natl. Acad. Sci. USA* 89, 2195–2199. 38.
Kato et al., *J Biol. Chem.*, 266(6):3361–3364, 1991.
Katzman, M. & Katz, R. A. (1999) *Adv. Vrirus Res.* 52, 371–395.
Lu, M., et al., (1992) *Biochemistry,* 31, 2455–2459.
M. E. (2000a) J. Biol. Chem. 275, 3421–3430.
Martin, *J Biol. Chem.* (1990) 265:20946–51.
Maurer, N., et al., (1999) *Mol. Membrane Biology* 16,129–140.
Mazumder, A. et al., (1996) *Biochemistry* 35, 13762–13771.
Molecular Cell Biology p641, Scientific American Books, W. H. Freeman and company, New York.
Mujoo et al., *J Biol. Chem.* (1986) 261:10299–305.
Nicolau and Sene, *Biochem. Biophys. Acta,* 721:185–190, 1982.
Nicolau et al., *Methods Enzymol.,* 149:157–176, 1987.
Pagnan et al., *Int J Cancer.* (1999) 81:268–74.
Pannecouque, et al., (1998) *Mol. Pharmacol.* 53, 340–345.
Perales et al., *Proc. Natl. Acad. Sci. USA,* 91:4086–4090, 1994.
Pommier, Y., Neamati, N., (1999) *Adv. Vrirus Res.* 52, 427–459.
Rando, F. R., et al., (1995) *Current Opinion Structural Biol.* 5: 311–322.
Rhodes, R. & Giraldo, R. (1995) *Current Opinion Structural Biol.* 5: 311–322.
Sen, D. & Gillbert, W. (1990) *Nature* 344, 410–414.

Spanjer H H, Scherphof G L. *Biochim Biophys Acta.* (1983) 734:40–7.

Szoka and Papahadjopoulos, *Proc. Natl. Acad. Sci.,* 75:4194–4198, 1978.

Templeton et al., *Nat Biotechnol.* (1997) 15:647–52.

Vakser, I A (1996) *Protein Eng.* 9, 37–41. 39

Wagner et al., *Science,* 260:1510–1513, 1990.

Williamson, J. R. (1994) *Annu. Rev. Biophys. Biomol. Structure* 23, 703–730.

Wong et al., *Gene.,* 10(2):87–94, 1980.

Wu and Wu, *J. Biol. Chem.,* 262:4429–4432, 1987.

Wu and Wu, *Adv. Drug Delivery Rev.,* 12:159–167, 1993.

Wyatt, J. R., et al. (1994) *Proc. Natl. Acad. Sci.* USA 91, 1356–1360.

What is claimed is:

1. A method of inhibiting hyperproliferative cell growth comprising administering to a cell an effective amount of a G-rich oligonucleotide which comprises SEQ ID NO. 2, which G-rich oligonucleotide forms a G-quartet structure and inhibits DNA binding activity of a signal transducer and activator of transcription 3 (STAT3) protein thereby inhibiting hyperproliferative cell growth.

2. The method of claim 1, wherein the cell is a tumor cell.

3. The method of claim 2, wherein the tumor cell is selected from the group consisting of a melanoma cell, a bladder cancer cell, a breast cancer cell, a lung cancer cell, a colon cancer cell, a prostate cancer cell, a liver cancer cell, a pancreatic cancer cell, a stomach cancer cell, a testicular cancer cell, a brain cancer cell, an ovarian cancer cell, a lymphatic cancer cell, a skin cancer cell, a brain cancer cell, a bone cancer cell, and a soft tissue cancer cell.

4. The method of claim 1 further comprising administering an antitumor agent.

5. The method of claim 4, wherein the antitumor agent is a chemotherapeutic drug.

6. A method of treating a hyperproliferative disease comprising administering to a patient an effective amount of a G-rich oligonucleotide which comprises SEQ. ID. NO. 2, which G-rich oligonucleotide forms a G-quartet structure and inhibits DNA binding activity of a signal transducer and activator of transcription 3 (STAT3) protein treating the hyperproliferative disease.

7. The method of claim 6, wherein the hyperproliferative disease is cancer.

8. The method of claim 7, wherein the cancer is selected from the group consisting of melanoma, bladder, non-small cell lung, small cell lung, lung, hepatocarcinoma, retinoblastoma, astrocytoma, glioblastoma, neuroblastoma, head, neck, breast, pancreatic, gum, tongue, prostate, renal, bone, testicular, ovarian, mesothelioma, cervical, gastrointestinal lymphoma, brain, and colon cancer.

9. The method of claim 6, wherein the hyperproliferative disease is selected from the group consisting of rheumatoid arthritis, inflammatory bowel disease, osteoarthritis, leiomyomas, adenomas, lipomas, hemangiomas, fibromas, vascular occlusion, restenosis, atherosclerosis, pre-neoplastic lesions, carcinoma in situ, oral hairy leukoplakia, and psoriasis.

10. The method of claim 6, wherein the patient is human.

11. A method of treating a hyperproliferative disease comprising administering to a patient an effective amount of a composition comprising a G-rich oligonucleotide which comprises SEQ. ID. NO. 2, which G-rich oligonucleotide forms a G-quartet structure and inhibits DNA binding activity of a signal transducer and activator of transcription 3 (STAT 3) protein, and which composition is administered in combination with chemotherapy, immunotherapy, surgery, or radiotherapy.

12. The method of claim 11, wherein the composition comprises a lipid-oligonucleotide complex.

13. The method of claim 11, wherein the hyperproliferative disease is cancer.

14. The method of claim 13, wherein the cancer is selected from the group consisting of melanoma, bladder, non-small cell lung, small cell lung, lung, hepatocarcinoma, retinoblastoma, astrocytoma, glioblastoma, neuroblastoma, head, neck, breast, pancreatic, gum, tongue, prostate, renal, bone, testicular, ovarian, mesothelioma, cervical, gastrointestinal lymphoma, brain, and colon cancer.

15. The method of claim 11, wherein the hyperproliferative disease is selected from the group consisting of rheumatoid arthritis, inflammatory bowel disease, osteoarthritis, leiomyomas, adenomas, lipomas, hemangiomas, fibromas, vascular occlusion, restenosis, atherosclerosis, pre-neoplastic lesions, carcinoma in situ, oral hairy leukoplakia, and psoriasis.

* * * * *

SEQUENCE LISTING

```
<160> NUMBER OF SEQ ID NOS: 7

<210> SEQ ID NO 1
<211> LENGTH: 16
<212> TYPE: DNA
<213> ORGANISM: Artificial Sequence
<220> FEATURE:
<223> OTHER INFORMATION: G-Quartet
<220> FEATURE:
<221> NAME/KEY: misc_structure
<222> LOCATION: (1)..(16)
<223> OTHER INFORMATION:

<400> SEQUENCE: 1
gggtgggtgg gtgggt                                                      16

<210> SEQ ID NO 2
<211> LENGTH: 16
<212> TYPE: DNA
<213> ORGANISM: Artificial Sequence
<220> FEATURE:
<223> OTHER INFORMATION: G-Quartet
<220> FEATURE:
<221> NAME/KEY: misc_structure
<222> LOCATION: (1)..(16)
<223> OTHER INFORMATION:

<400> SEQUENCE: 2
gggcgggcgg gcgggc                                                      16

<210> SEQ ID NO 3
<211> LENGTH: 24
<212> TYPE: DNA
<213> ORGANISM: Artificial Sequence
<220> FEATURE:
<223> OTHER INFORMATION: G-Quartet
<220> FEATURE:
<221> NAME/KEY: misc_structure
<222> LOCATION: (1)..(24)
<223> OTHER INFORMATION:

<400> SEQUENCE: 3
gggggtgggg gtgggggtggg ggt                                             24

<210> SEQ ID NO 4
<211> LENGTH: 16
<212> TYPE: DNA
<213> ORGANISM: Artificial Sequence
<220> FEATURE:
<223> OTHER INFORMATION: G-Quartet
<220> FEATURE:
<221> NAME/KEY: misc_structure
<222> LOCATION: (1)..(16)
<223> OTHER INFORMATION:

<400> SEQUENCE: 4
gggcgggtgg gtgggt                                                      16
```

```
<210> SEQ ID NO 5
<211> LENGTH: 16
<212> TYPE: DNA
<213> ORGANISM: Artificial Sequence
<220> FEATURE:
<223> OTHER INFORMATION: G-Quartet
<220> FEATURE:
<221> NAME/KEY: misc_structure
<222> LOCATION: (1)..(16)
<223> OTHER INFORMATION:

<400> SEQUENCE: 5
gggtgggtgg gcgggt                                                  16

<210> SEQ ID NO 6
<211> LENGTH: 23
<212> TYPE: DNA
<213> ORGANISM: Artificial Sequence
<220> FEATURE:
<223> OTHER INFORMATION: Unknown
<220> FEATURE:
<221> NAME/KEY: misc_feature
<222> LOCATION: (1)..(23)
<223> OTHER INFORMATION:

<400> SEQUENCE: 6
agcttcattt cccgtaaatc cta                                          23

<210> SEQ ID NO 7
<211> LENGTH: 20
<212> TYPE: DNA
<213> ORGANISM: Artificial Sequence
<220> FEATURE:
<223> OTHER INFORMATION: Unknown
<220> FEATURE:
<221> NAME/KEY: misc_feature
<222> LOCATION: (1)..(20)
<223> OTHER INFORMATION:

<400> SEQUENCE: 7
tgccggatca agagctacca                                              20
```